United States Patent
Natrajan et al.

(10) Patent No.: US 8,119,422 B2
(45) Date of Patent: Feb. 21, 2012

(54) STABLE ACRIDINIUM ESTERS WITH FAST LIGHT EMISSION

(75) Inventors: Anand Natrajan, Manchester, NH (US); Qingping Jiang, East Walpole, MA (US); David Sharpe, Foxborough, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 375 days.

(21) Appl. No.: 12/445,304

(22) PCT Filed: Oct. 15, 2007

(86) PCT No.: PCT/US2007/081375
§ 371 (c)(1), (2), (4) Date: Apr. 13, 2009

(87) PCT Pub. No.: WO2008/067055
PCT Pub. Date: Jun. 5, 2008

(65) Prior Publication Data
US 2010/0099077 A1    Apr. 22, 2010

Related U.S. Application Data

(60) Provisional application No. 60/829,363, filed on Oct. 13, 2006.

(51) Int. Cl.
*G01N 33/533* (2006.01)
*G01N 21/76* (2006.01)
*C07D 219/00* (2006.01)

(52) U.S. Cl. ............ 436/546; 435/7.1; 436/56; 436/172; 546/102

(58) Field of Classification Search ....................... None
See application file for complete search history.

(56) References Cited

U.S. PATENT DOCUMENTS 5,595,875 A    1/1997  Law et al.
5,756,709 A    5/1998  Nelson et al.

FOREIGN PATENT DOCUMENTS

EP    0263657 A2    4/1988

*Primary Examiner* — Shafiqul Haq

(57) ABSTRACT

Chemiluminescent acridinium esters are provided which are fast light emitting and hydrolytically stable. The chemiluminescent acridinium esters are useful labels in assays for detecting or quantifying analytes.

23 Claims, 2 Drawing Sheets

R1 = Me, DMAE-NHS
R1 = -CH$_2$CH$_2$CH$_2$SO$_3^-$, NSP-DMAE-NHS

General structure of an acridinium sulfonamide (R2 and R3 are alkyl or aryl groups)

STABLE ACRIDINIUM ESTERS WITH FAST LIGHT EMISSION

FIELD OF INVENTION

The present invention relates generally to chemiluminescent acridinium esters useful as labels in immunoassasays and the like. The chemiluminescent acridinium esters are hydrolytically stable and fast light emitting.

BACKGROUND OF THE INVENTION

Chemiluminescent acridinium compounds are extremely useful labels that have been used extensively in immunoassays and nucleic acid assays. A recent review, Pringle, M. J., *Journal of Clinical Ligand Assay* vol. 22, pp. 105-122 (1999) summarizes past and current developments in this class of chemiluminescent compounds.

Seminal work by McCapra, F. et al., *Tetrahedron Lett.* vol. 43, pp. 3167-3172 (1964) and Rahut et al. *J. Org. Chem* vol. 301, pp. 3587-3592. (1965) disclosed that chemiluminescence from phenyl esters of acridinium salts could be triggered by alkaline peroxide. Since these early studies, interest in acridinium compounds has increased because of their utility as chemiluminescent labels. The application of the acridinium ester, 9-carboxyphenyl-N-methylacridinium bromide in an immunoassay was disclosed by Simpson, J. S. A. et al., *Nature* vol. 279, pp. 646-647 (1979). This acridinium ester is quite unstable owing to hydrolysis of the ester linkage between the acridinium ring and the phenol thereby limiting its commercial utility unless special precautions are taken to protect the ester linkage from hydrolysis. For example Arnold et al. in U.S. Pat. No. 4,950,613 have shown that the hydrolytic stability of unstable acridinium esters can be alleviated somewhat with additives.

Different strategies for increasing the hydrolytic stability of acridinium compounds by altering their structures have been described. Law et al., *Journal of Bioluminescence and Chemiluminescence*, vol. 4, pp. 88-89 (1989) reported that phenols containing two methyl groups flanking the phenolic group afforded acridinium esters that are more resistant to hydrolysis. The acridinium ester DMAE-NHS [2',6'-dimethyl-4'-(N-succinimidyloxycarbonyl)phenyl 10-methylacridinium-9-carboxylate] was found to have the same light output as an acridinium ester lacking the two methyl groups but was significantly more resistant to hydrolysis. U.S. Pat. Nos. 4,918,192 and 5,110,932 describe DMAE and its applications. U.S. Pat. No. 5,656,426 to Law et al. discloses a hydrophilic version of DMAE termed NSP-DMAE-NHS ester where the methyl group on the acridinium ring nitrogen is replaced with a sulfopropyl group. Natrajan et al. in U.S. Pat. No. 6,664,043 B2 disclosed NSP-DMAE derivatives with hydrophilic modifiers attached to the phenol.

A different class of stable chemiluminescent acridinium compounds has been described by Kinkel et al., *Journal of Bioluminescence and Chemiluminescence* vol. 4, pp. 136-139 (1989) and Mattingly, *Journal of Bioluminescence and Chemiluminescence* vol. 6, pp. 107-114 (1991) and U.S. Pat. No. 5,468,646. In this class of compounds, the phenolic ester linkage is replaced by a sulfonamide moiety, which is reported to impart hydrolytic stability without compromising the light output. The structure of DMAE-NHS and the generalized structure of an acridinium sulfonamide are illustrated in FIG. 1 along with the numbering system commonly used for acridinium ester. The phenol and the sulfonamide moieties are also commonly referred to as leaving groups. Chemiluminescent acridinium compounds containing other leaving groups such as oximes have also been disclosed. See Renotte et al. *Luminescence* 2000, 15, 311-320.

Acridinium compounds, in aqueous solution, exist in equilibrium with adducts formed by the addition of water to C-9 of the acridinium ring. This adduct is commonly referred to as the pseudobase. The acridinium-pseudobase equilibrium, which is illustrated in FIG. 2, is strongly influenced by the pH of the aqueous medium. In acidic solutions the acridinium form is favored whereas in basic solution, the predominant form is the pseudobase. The acridinium-pseudobase equilibrium is also affected by the structure of the acridinium compound. Acridinium esters containing electron-donating groups at C-2 and/or C-7, reduce the electrophilicity of C-9 and raise the pH at which the transition from the acridinium form to the pseudobase takes place. Acridinium sulfonamides also are less prone to pseudobase formation than acridinium esters.

Chemiluminescence from acridinium compounds is normally triggered with hydrogen peroxide. The mechanism of light emission is believed to involve addition of hydrogen peroxide to C-9 of the acridinium ring followed by cleavage of the leaving group and concomitant formation of a high energy, dioxetanone intermediate. Rapid decomposition of the dioxetanone intermediate is presumed to lead to formation of the acridone in an electronically excited state. Light emission occurs when the acridone in the excited state reverts to the ground state. The formation of the dioxetanone intermediate has not been demonstrated conclusively and, a recent theoretical study postulates that cleavage of the leaving group and formation of the excited state acridone may occur simultaneously. (Rak et al. *J. Org. Chem.* 1999, 64, 3002-3008).

In practice, light emission from acridinium compounds and their conjugates using hydrogen peroxide is normally accomplished by an initial treatment with aqueous acid to effect complete conversion of the pseudobase to the acridinium form followed by the addition of aqueous base. Acid treatment is necessary because the pseudobase cannot react with hydrogen peroxide. The length of acid treatment and the strength of the acid that must be used depend upon the structure of the acridinium compound. The addition of base ionizes the hydrogen peroxide molecule to form the hydroperoxide ion, which then adds to C-9 of the acridinium ring and initiates light emission. For convenience, hydrogen peroxide is often added along with the aqueous acid as a single reagent. Typically, light emission from the acridinium compound or its conjugate occurs over a time period of a few seconds.

The kinetics or the rate of light emission from the acridinium compound or its conjugate depends on a number of factors. Both the concentrations of hydrogen peroxide as well as that of the base can affect the duration of light emission. The presence of surfactants can also affect the rate of light emission as well as the quantum yield. In addition, the structure of the acridinium compound also has a profound effect on the kinetics of light emission. Although substituents on the acridinium ring, at the acridinium nitrogen and on the leaving group can all affect the kinetics of light emission, the impact of various structural features of the leaving group on light emission has been most widely reported. For example, Adamczyk et al. (*Tetrahedron* 1999, 55, 10899-10914) from a study of various acridinium sulfonamides have shown that the kinetics of light emission can be varied by structural variation of the sulfonamide leaving group without affecting the total amount of light emitted by these compounds. These investigators concluded from their study that steric factors were more influential in varying the rate of light emission than the pKa of the sulfonamide leaving group. Increasing steric congestion at the acridinium sulfonamide nitrogen led to slow light emission while relieving such steric hindrance speeded up light emission.

A similar study on acridinium phenyl esters was reported by Nelson et al. (*Biochemistry* 1996, 35, 8429-8438). From their study, the authors concluded that the pKa of the phenol leaving group had a more significant impact on the kinetics of light emission than steric effects. Electron withdrawing groups on the phenyl ring led to an acceleration in the rate of light emission while electron-donating groups led to a suppression of the rate. The acridinium esters described by Nelson are quite susceptible to hydrolysis even though they show fast light emission. The 'hybridization protection assays' described by Nelson, in fact, take advantage of the fact that acridinium esters conjugated to nucleic acid probes and, not hybridized to their targets, can be hydrolyzed at much faster rates that the labeled hybridized probes.

Steric effects also play an important role in the kinetics of light emission of acridinium phenyl esters. For example Woodhead et al. in U.S. Pat. No. 5,656,207 have reported that the kinetics of light emission of an acridinium ester containing methyl groups at the 2' and 6' carbon atoms on the phenol can be differentiated from an analogous acridinium ester lacking these two substituents by a careful selection of the light triggering reagents.

Acridinium esters containing methyl groups at the 2' and 6' carbons emit light more slowly than acridinium esters lacking these substituents. On the other hand, the presence of the methyl groups imparts much greater hydrolytic stability on the acridinium ester as noted by Law et al., (*Journal of Bioluminescence and Chemiluminescence*, vol. 4, pp. 88-89 (1989) who compared the hydrolytic stability of DMAE-NHS with an analogous acridinium ester lacking the 2' and 6' methyl groups. Hydrolytic stability is important especially for commercial applications of acridinium esters in automated immunochemistry instruments because it is tied to reagent stability. Reagents with a long shelf are often preferred because they cause less day-to-day variations in assay performance and do not create as much waste.

Hydrolytically stable acridinium esters such as NSP-DMAE described in U.S. Pat. No. 5,656,426 when conjugated to proteins or small molecules, typically emit light over a period of five seconds when their chemiluminescence is triggered with alkaline peroxide.

In view of the foregoing, there is a need in the art for acridinium esters which exhibit both hydrolytic stability and fast light emission. It is therefore and object of the invention to provide acridinium esters which are hydrolytically stable, e.g., comparable to NSP-DMAE, but which also exhibit much faster light emission, that is, on the order of one to two seconds.

SUMMARY OF THE INVENTION

The present invention is founded on the discovery that the rate of light emission from acridinium esters can surprisingly be increased without compromising their hydrolytic stability. The acridinium esters of the present invention have novel structural features which distinguish them from the fast light emitting acridinium esters described above which typically are hydrolytically unstable. The inventive acridinium esters thus offer considerable advantages over unsubstituted acridinium phenyl esters, which are quite susceptible to hydrolysis even though they show fast light emission.

In one aspect of the invention, hydrolytically stable, fast light emitting chemiluminescent acridinium compounds comprising the structure of Formula I are provided:

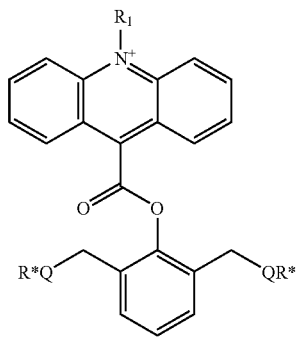

wherein Q is selected independently at each occurrence from a bond (i.e., Q is not present) or a heteroatom or heteroatom containing group, selected from —O—, —S—, or —N(R*)—; wherein R* is selected independently at each occurrence from hydrogen, substituted or unsubstituted, branched or straight chain alkyl, alkenyl, alkynyl, aryl, alkyl-aryl, or aryl-alkyl, and combinations thereof, optionally containing from one to 20 heteroatoms selected from the group consisting of oxygen, nitrogen, phosphorous, sulfur, halogen, and combinations thereof; with the proviso that at least one Q must be —O—, —S—, or —N(R*)—; and wherein $R_1$ is an alkyl, alkenyl, alkynyl, aryl-alkyl or alkyl-aryl group containing up to 20 heteroatoms.

In another aspect of the invention, hydrolytically stable, fast light emitting chemiluminescent acridinium compounds comprising the structure of Formula II are provided:

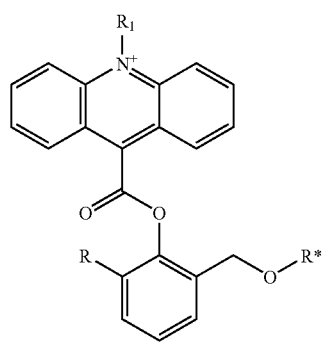

wherein R and R* are selected independently from hydrogen, substituted or unsubstituted, branched or straight chain alkyl, alkenyl, alkynyl, aryl, alkyl-aryl, or aryl-alkyl, and combinations thereof, optionally containing from one to 20 heteroatoms selected from the group consisting of oxygen, nitrogen, phosphorous, sulfur, halogen, and combinations thereof; and wherein $R_1$ is as defined above.

In yet another aspect of the invention, hydrolytically stable, fast light emitting chemiluminescent acridinium compounds comprising the structure of Formula III are provided:

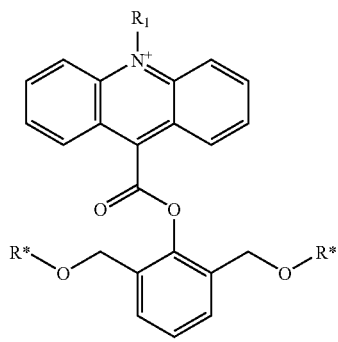

III wherein R* is selected independently at each occurrence from hydrogen, substituted or unsubstituted, branched or straight chain alkyl, alkenyl, alkynyl, aryl, alkyl-aryl, or aryl-alkyl, and combinations thereof, optionally containing from one to 20 heteroatoms selected from the group consisting of oxygen, nitrogen, phosphorous, sulfur, halogen, and combinations thereof; and wherein $R_1$ is as defined above.

In a further aspect of the invention, hydrolytically stable, fast light emitting chemiluminescent acridinium compounds of Formula IV are provided:

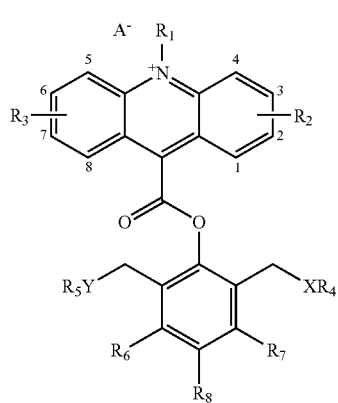

IV wherein, $R_1$ is an alkyl, alkenyl, alkynyl, aryl-alkyl or alkyl-aryl group containing up to 20 heteroatoms; and preferably $R_1$ is a methyl, a sulfopropyl, or a sulfobutyl group;

$R_2$ is a functional group at any of C1 to C4 and $R_3$ is functional group at any of C5 to C8, wherein $R_2$ and $R_3$ are independently selected from hydrogen, alkyl, alkenyl, alkynyl, aryl, aryl-alkyl or alkyl-aryl groups containing up to 20 heteroatoms selected from oxygen, nitrogen, sulfur or halogen;

X and Y are selected independently at each occurrence from a bond, —O—, —S—, or —N(R*)—; wherein R* is selected independently at each occurrence from hydrogen, substituted or unsubstituted, branched or straight chain alkyl, alkenyl, alkynyl, aryl, alkyl-aryl, or aryl-alkyl, and combinations thereof, optionally containing from one to 20 heteroatoms selected from the group consisting of oxygen, nitrogen, phosphorous, sulfur, halogen, and combinations thereof; with the proviso that either X or Y or both must be —O—, —S—, or —N(R*)—;

$R_4$, and $R_5$ are independently selected from hydrogen, alkyl, alkenyl, alkynyl, aryl, aryl-alkyl or alkyl-aryl groups containing up to 20 heteroatoms selected from oxygen, nitrogen, sulfur or halogen;

$R_6$ and $R_7$ are independently selected from hydrogen, alkyl, alkenyl, alkynyl, aryl-alkyl, alkyl-aryl, alkoxyl (—OR), alkylthiol (—SR), and —$NR_2$ groups where R on the nitrogen can be the same or different, R is an alkyl, alkenyl, alkynyl, aryl, aryl-alkyl or alkyl-aryl group containing up to 20 heteroatoms, $R_8$ is exchangeable with $R_6$ and $R_7$ and is a group —$R_9$-$R_{10}$, where $R_9$ represents a bond or a substituted or unsubstituted, branched or straight-chain alkyl, aryl, aryl-alkyl or alkyl-aryl group containing up to 20 heteroatoms, and $R_{10}$ is a electrophilic or nucleophilic functional group selected from the following:

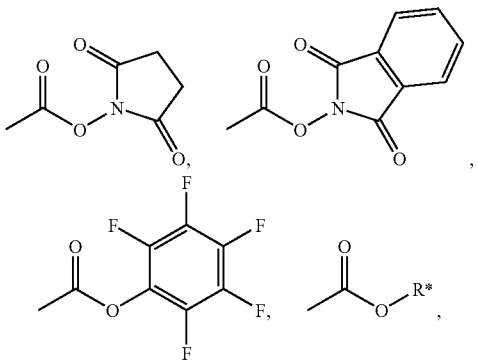

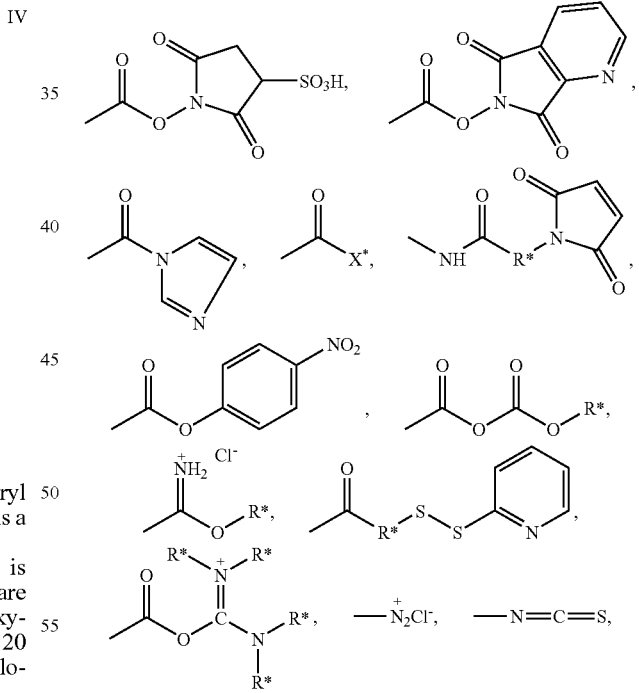

—$N_3$, —$SO_2Cl$, —NCO, —$NH_2$, —SH, —OH, —NH—$NH_2$, and —O—$NH_2$;

wherein X* is a halogen; and R* is selected from the group consisting of hydrogen, substituted or unsubstituted, branched or straight chain alkyl, alkenyl, alkynyl, aryl, alkyl-aryl, or aryl-alkyl, and combinations thereof, optionally containing one or more heteroatoms selected from the group consisting of oxygen, nitrogen, phosphorous, sulfur, halogen, and combinations thereof; and A⁻ is a counter ion which is introduced to pair with the quaternary nitrogen of said acridinium nucleus, and is selected from the group consisting of $CH_3SO_4^-$, $FSO_3^-$, $CF_3SO_4^-$, $C_4F_9SO_4^-$, $CH_3C_6H_4SO_3^-$, halide, $CF_3COO^-$, $CH_3COO^-$, and $NO_3^-$.

The invention also provides assay for the detection or quantification of an analyte. In another aspect of the invention, an assay for the detection or quantification of an analyte comprises the following steps:

(a) providing a conjugate comprising: (i) a binding molecule specific for an analyte; and (ii) a hydrolytically stable, fast light emitting acridinium ester comprising the structure of Formula I or Formula II;

(b) providing a solid support having immobilized thereon a second binding molecule specific for said analyte;

(c) mixing the conjugate, the solid phase and a sample suspected of containing the analyte to form a binding complex;

(d) separating the binding complex captured on the solid support;

(e) triggering chemiluminescence of the binding complex from step (d) by adding chemiluminescence triggering reagents;

(f) measuring the amount of light emission with a luminometer; and (g) detecting the presence or calculating the concentration of the analyte by comparing the amount of light emitted from the reaction mixture with a standard dose response curve which relates the amount of light emitted to a known concentration of the analyte.

In another aspect of the invention, an assay for the detection or quantification of an analyte is provided comprising the steps of:

(a) providing a conjugate of an analyte with a hydrolytically stable, fast light emitting acridinium ester comprising the structure of Formula I or Formula II;

(b) providing a solid support immobilized with a binding molecule specific for the analyte;

(c) mixing the conjugate, solid support and a sample suspected of containing the analyte to form a binding complex;

(d) separating the binding complex captured on the solid support;

(e) triggering the chemiluminescence of the binding complex from step (d) by adding chemiluminescence triggering reagents;

(f) measuring the amount of light with an luminometer; and (g) detecting the presence or calculating the concentration of the analyte by comparing the amount of light emitted from the reaction mixture with a standard dose response curve which relates the amount of light emitted to a known concentration of the analyte.

These and other aspects of the present invention will become apparent to those skilled in the art after a reading of the following detailed description of the invention, including the illustrative embodiments, examples, and Figures.

DETAILED DESCRIPTION

Figure 1:
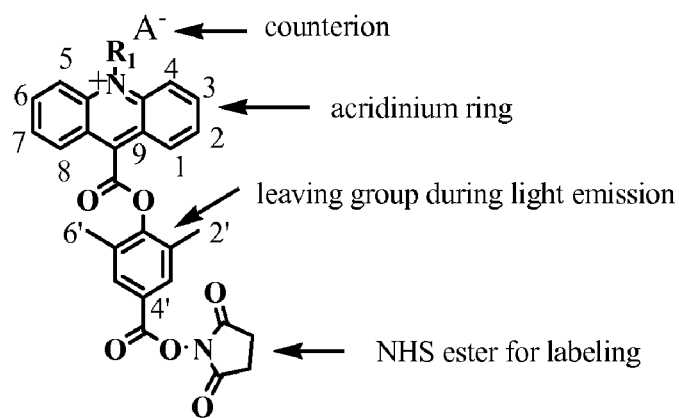
FIG. 1 shows the structure of the acridinium esters DMAE-NHS and NSP-DMAE-NHS along with the numbering system commonly used for acridinium esters. The generalized structure of an acridinium sulfonamide is also shown.
Figure 1:
Figure 2:
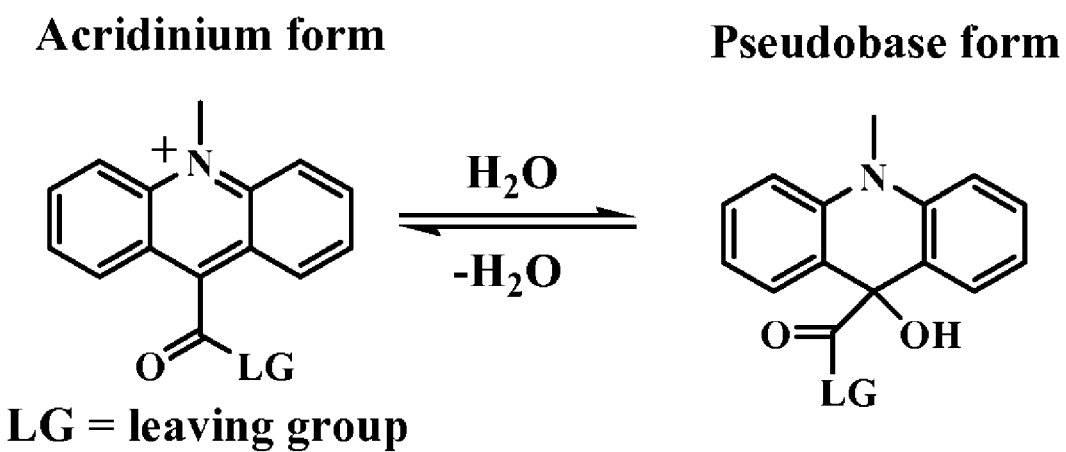
FIG. 2 illustrates the equilibrium between the acridinium form and the pseudobase form of an acridinium compound.

As used herein all terms have their ordinary meaning in the art unless explicitly defined.

By "chemiluminescent acridinium compound comprising the structure" of Formula I or Formula II is meant that the chemiluminescent acridinium compound includes as part or all of its structure the structure of Formula I or II, and therefore includes compounds where the specified structure optionally contains one or more additional substituents at any available position of the acridinium nucleus, including the ring nitrogen, and phenyl ring, as well as salts thereof. The substituents may be selected from, for example, substituted or unsubstituted, branched or straight chain alkyl, alkenyl, alkynyl, aryl, alkyl-aryl, or aryl-alkyl, and combinations thereof, typically containing from one to 50 carbon atoms, and optionally containing from one to 20 heteroatoms selected from the group consisting of oxygen, nitrogen, phosphorous, sulfur, halogen, and combinations thereof. Exemplary substituents include without limitation, branched or straight chain $C_1$-$C_{20}$ alkyl, alkenyl, or alkynyl group, including without limitation methyl, ethyl, propyl, isopropyl, butyl, isobutyl, t-butyl, n-pentyl, iso-pentyl, neo-pentyl, tert-pentyl, hexyl, vinyl, allyl, butenyl, pentenyl, hexenyl, propynyl, butynyl, pentynyl; cycloalkyl, heterocycloalkyl, haloalkyl, benzyl, alkyl-aryl; substituted or unsubstituted aryl or heteroaryl groups; acyl, amino, alkyl amino, dialkyl amino, hydroxyl, alkoxy, carboxy, carbamide, cyano, oxo, oxa, halogen, and the like, and combinations thereof, optionally including additional substitution with one or more hetero atoms, including, oxygen, nitrogen, phosphorous, sulfur, halogen, and combinations thereof.

By "fast light emitting" is meant, in the case of the acridinium esters in a free state (i.e., not conjugated to another molecule) that at least about 90% of the total yield of light from the chemiluminescent reaction is produced within two seconds of base addition; and in the case of acridinium ester conjugates, that at least about 90% of the total yield of light from the chemiluminescent reaction is produced within one second of base addition, under the conditions specified herein.

The term "small molecule" refers to any organic molecule having a molecular weight of less than about 3,000, preferably less than about 2,000, and more preferable less than about 1,000 daltons.

The acridinium compounds of the present invention achieve fast light emission and hydrolytic stability through the presence of heteroatoms on the methylene carbons of the phenyl ring. In one embodiment, the hydrolytically stable, fast light emitting chemiluminescent acridinium compound comprises the structure of Formula I:

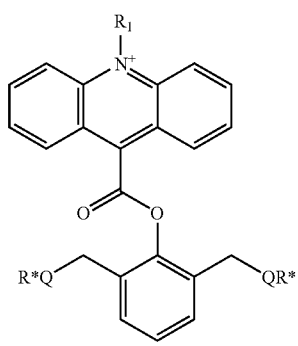

wherein Q is selected independently at each occurrence from a bond, —O—, —S—, or —N(R*)—; wherein R* is selected independently at each occurrence from hydrogen, substituted or unsubstituted, branched or straight chain alkyl, alkenyl, alkynyl, aryl, alkyl-aryl, or aryl-alkyl, and combinations thereof, optionally containing from one to 20 heteroatoms selected from the group consisting of oxygen, nitrogen, phosphorous, sulfur, halogen, and combinations thereof; with the proviso that at least one Q must be —O—, —S—, or —N(R*)—. In a preferred embodiment, one or both Q substituents are —O—. $R_1$ is an alkyl, alkenyl, alkynyl, arylalkyl or alkyl-aryl group containing up to 20 heteroatoms. Preferably, $R_1$ is a methyl group or a sulfo-alkyl group, including without limitation sulfopropyl and sulfobutyl groups.

Without wishing to be bound by any particular theory, it is believed that when a heteroatom having at least one pair of non bonding electrons (i.e., a "lone pair"), such as —O—, —S—, or —N(R*)—, and in particular —O—, is attached directly to either or both of the methylene substituents on carbons 2' and 6' of the phenyl ring, the heteroatom acts as a base to catalyze the chemiluminescent reaction of the acridinium ester with peroxide.

In another embodiment, the hydrolytically stable, fast light emitting chemiluminescent acridinium compound comprises the structure of Formula II:

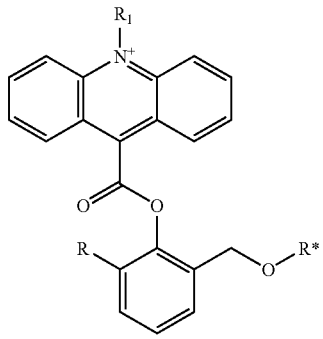

II wherein R and R* are selected independently from hydrogen, substituted or unsubstituted, branched or straight chain alkyl, alkenyl, alkynyl, aryl, alkyl-aryl, or aryl-alkyl, and combinations thereof, optionally containing from one to 20 heteroatoms selected from the group consisting of oxygen, nitrogen, phosphorous, sulfur, halogen, and combinations thereof; and wherein $R_1$ is defined as above. In a preferred embodiment R is an optionally substituted $C_1$-$C_5$ alkyl group, preferably methyl.

In another embodiment, the hydrolytically stable, fast light emitting chemiluminescent acridinium compound comprises the structure of Formula III:

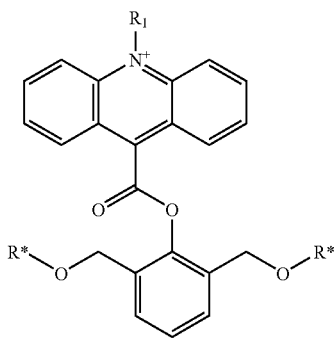

III wherein R* is selected independently at each occurrence from hydrogen, substituted or unsubstituted, branched or straight chain alkyl, alkenyl, alkynyl, aryl, alkyl-aryl, or aryl-alkyl, and combinations thereof, optionally containing from one to 20 heteroatoms selected from the group consisting of oxygen, nitrogen, phosphorous, sulfur, halogen, and combinations thereof; and wherein $R_1$ is defined as above.

In another embodiment of the invention, the hydrolytically stable, fast light emitting chemiluminescent acridinium compound has the structure of Formula IV are provided:

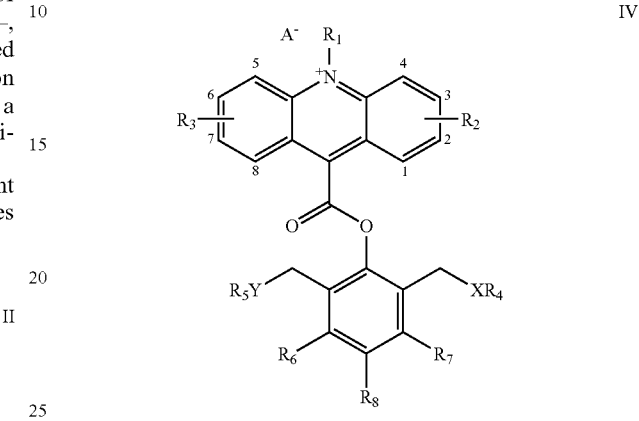

IV wherein each of the specified substituents is defined as follows.

$R_1$ is an alkyl, alkenyl, alkynyl, aryl-alkyl or alkyl-aryl group containing up to 20 heteroatoms; and preferably $R_1$ is a methyl, a sulfopropyl, or a sulfobutyl group.

$R_2$ is a functional group at any of $C_1$ to $C_4$ and $R_3$ is functional group at any of $C_5$ to $C_8$, wherein $R_2$ and $R_3$ are independently selected from hydrogen, alkyl, alkenyl, alkynyl, aryl, aryl-alkyl or alkyl-aryl groups containing up to 20 heteroatoms selected from oxygen, nitrogen, sulfur or halogen. It will be understood that the heteroatoms may comprise any part of the alkyl, alkenyl, alkynyl, aryl, aryl-alkyl or alkyl-aryl groups and therefore may form part of the backbone of the group, as in, for example, alkoxy, ether, or a heteroaryl group, or the heteroatom or heteroatoms containing group may be pendent from the alkyl, alkenyl, alkynyl, aryl, aryl-alkyl or alkyl-aryl groups, as in the case of a ketone, halogen, or the like. Specifically, contemplated heteroatom substitutions include those where $R_2$ and/or $R_3$ are connected to the acridinium nucleus through an oxygen atom (i.e., $R_2$ and/or $R_3$ are alkoxy substituents) and those where $R_2$ and/or $R_3$ further comprise an ether, or polyether structure, including, for example, polyethers of the general form —($CH_2$—$CH_2$—O)$_n$—. In one interesting variant, the polyether is linked to the acridinium ring through an oxygen and $R_2$ and/or $R_3$ thus is of the form —O—($CH_2$—$CH_2$—O)$_n$—. The polyether may be terminated by any group, including alkyl, alkenyl, alkynyl, aryl, aryl-alkyl or alkyl-aryl groups. In a preferred embodiment $R_2$ and/or $R_3$ will have the form —O—($CH_2$—$CH_2$—O)$_n$—$CH_3$ where n is an integer between 1 and 20, preferably between 1 and 10.

X and Y are independently selected from a bond (i.e., the group is not present and therefore $R_4$ and $R_5$ are attached directly to the acridinium nucleus), oxygen, sulfur or nitrogen. In preferred embodiments at least one of X and Y is —O—. In the case where X and/or Y are nitrogen atoms, the nitrogen atom may form, together with the acridinium nucleus and $R_4$ and/or $R_5$, a secondary amine, or the nitrogen atom may together with the acridinium nucleus and $R_4$ and/or $R_5$ and a group R*, form a tertiary amine, where R* is a group as defined herein.

$R_4$ and $R_5$ are independently selected from hydrogen, alkyl, alkenyl, alkynyl, aryl, aryl-alkyl or alkyl-aryl groups containing up to 20 heteroatoms selected from oxygen, nitrogen, sulfur or halogen. $R_4$ and/or $R_5$ may, for example, comprise an ether, or polyether structure, including, for example, polyethers of the general form $-(CH_2-CH_2-O)_n-$. In one interesting variant, where X and/or Y is $-O-$, the polyether is linked to the acridinium ring through an oxygen to form, together with X and/or Y, a radical of the type $-O-(CH_2-CH_2-O)_n-$. The polyether may be terminated by any group, including alkyl, alkenyl, alkynyl, aryl, aryl-alkyl or alkyl-aryl groups. In a preferred embodiment $R_4$ and/or $R_5$ will have the form $-(CH_2-CH_2-O)_n-CH_3$ where n is an integer between 1 and 20, preferably between 1 and 10, and together with X and/or Y will form a group $-O-(CH_2-CH_2-O)_n-CH_3$. Other suitable substituents for $R_4$ and $R_5$ include, without limitation, $C_1-C_{10}$ branched or straight chain alkyl, such as methyl, ethyl, propyl, isopropyl, butyl, isobutyl, tert-butyl, and the like, optionally comprising any number of heteroatoms, preferably oxygen atoms, which when present may comprise, for example, ether or polyether functionalities.

$R_6$ and $R_7$ are independently selected from hydrogen, alkyl, alkenyl, alkynyl, aryl-alkyl, alkyl-aryl, alkoxyl ($-OR$), alkylthiol ($-SR$), and $-NR_2$ groups where R on the nitrogen can be the same or different, R is an alkyl, alkenyl, alkynyl, aryl, aryl-alkyl or alkyl-aryl group containing up to 20 heteroatoms.

$R_8$ is a group $-R_9-R_{10}$, where $R_9$ represents a bond or a substituted or unsubstituted, branched or straight-chain alkyl, aryl, aryl-alkyl or alkyl-aryl group containing up to 20 heteroatoms, and $R_{10}$ is a electrophilic or nucleophilic functional group selected from the following:

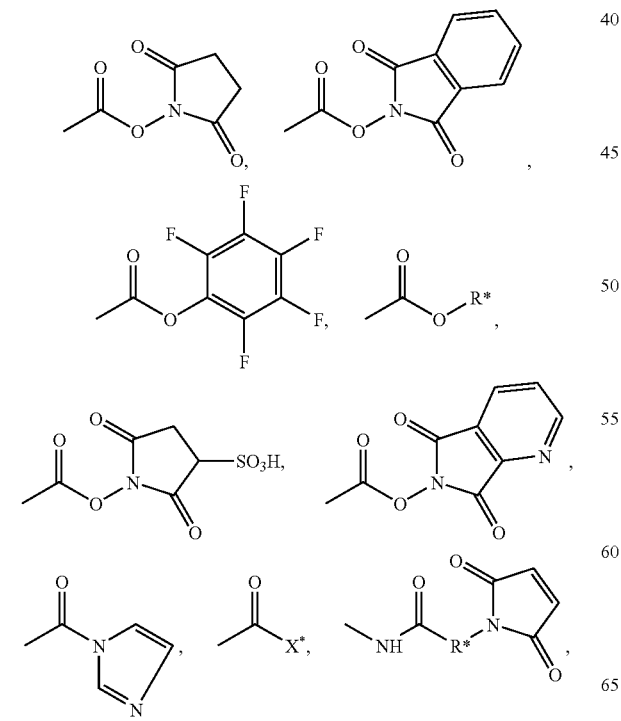
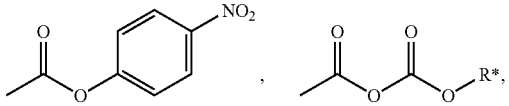
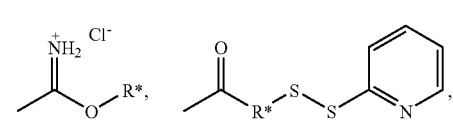
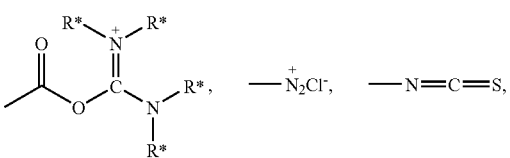

$-N_3$, $-SO_2Cl$, $-NCO$, $-NH_2$, $-SH$, $-OH$, $-NH-NH_2$, and $-O-NH_2$;

wherein X* is a halogen; and R* is selected from the group consisting of hydrogen, substituted or unsubstituted, branched or straight chain alkyl, alkenyl, alkynyl, aryl, alkyl-aryl, or aryl-alkyl, and combinations thereof, optionally containing one or more heteroatoms selected from the group consisting of oxygen, nitrogen, phosphorous, sulfur, halogen, and combinations thereof; and $A^-$ is a counter ion which is introduced to pair with the quaternary nitrogen of said acridinium nucleus, and is selected from the group consisting of $CH_3SO_4^-$, $FSO_3^-$, $CF_3SO_4^-$, $C_4F_9SO_4^-$, $CH_3C_6H_4SO_3^-$, halide, $CF_3COO^-$, $CH_3COO^-$, and $NO_3^-$.

Particularly interesting acridinium esters of the present invention have the following structure:

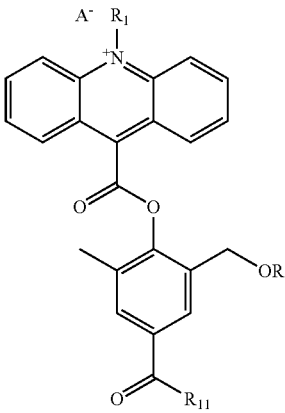

where $R_1$ is -Me or $-CH_2CH_2CH_2SO_3^-$;

R is an alkyl, alkenyl, alkynyl, aryl, aryl-alkyl or alkyl-aryl group containing up to 20 heteroatoms, $R_{11}$ is $-OH$, $-O-N$-succinimidyl, $-NH-(CH_2)_5-C(O)-O-N$-succinimidyl, $-NH-(C_2H_4O)_n-C_2H_4NH-C(O)-O-N$-succinimidyl wherein n=0 to 5, or $-NH-R-NHR$ and where $A^-$ is as described previously.

Exemplary acridinium esters of the present invention include, without limitation, the following:

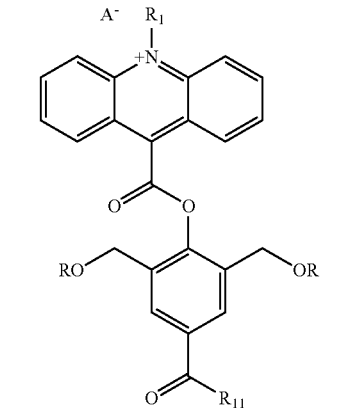

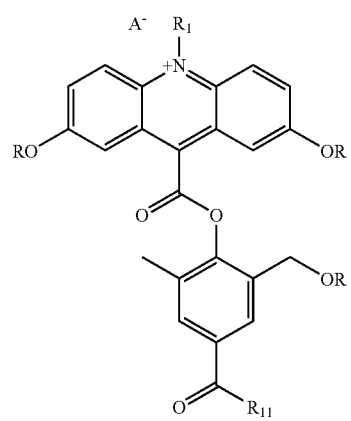

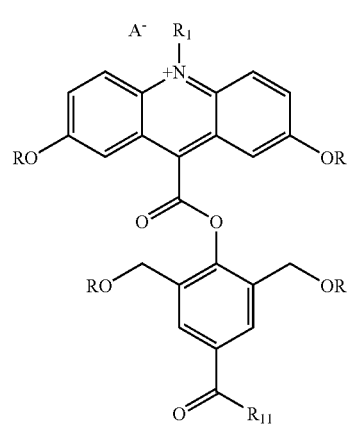

where $R_1$, R, $R_{11}$ and $A^-$ are the same as described previously.

The acridinium esters of the present invention may also have the following structure:

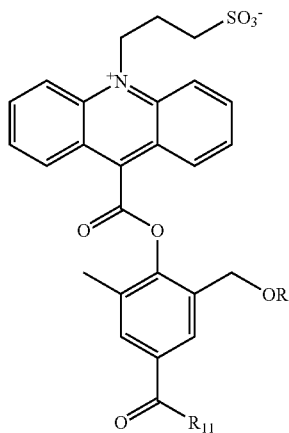

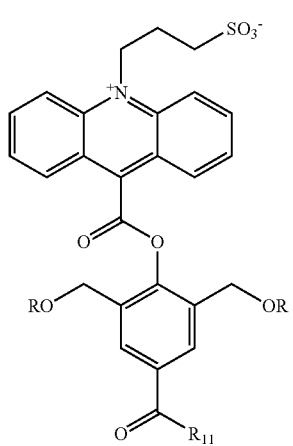

where R is selected from -Me, —$CH_2CH_2OMe$, —$CHMe_2$ and —$(CH_2CH_2O)_nCH_2CH_2OMe$, —$CH[CH_2O(CH_2CH_2O)_nCH_2CH_2OMe]_2$, n=1-5 and $R_{11}$ is as described previously.

Other exemplary acridinium esters of the present invention include the following:

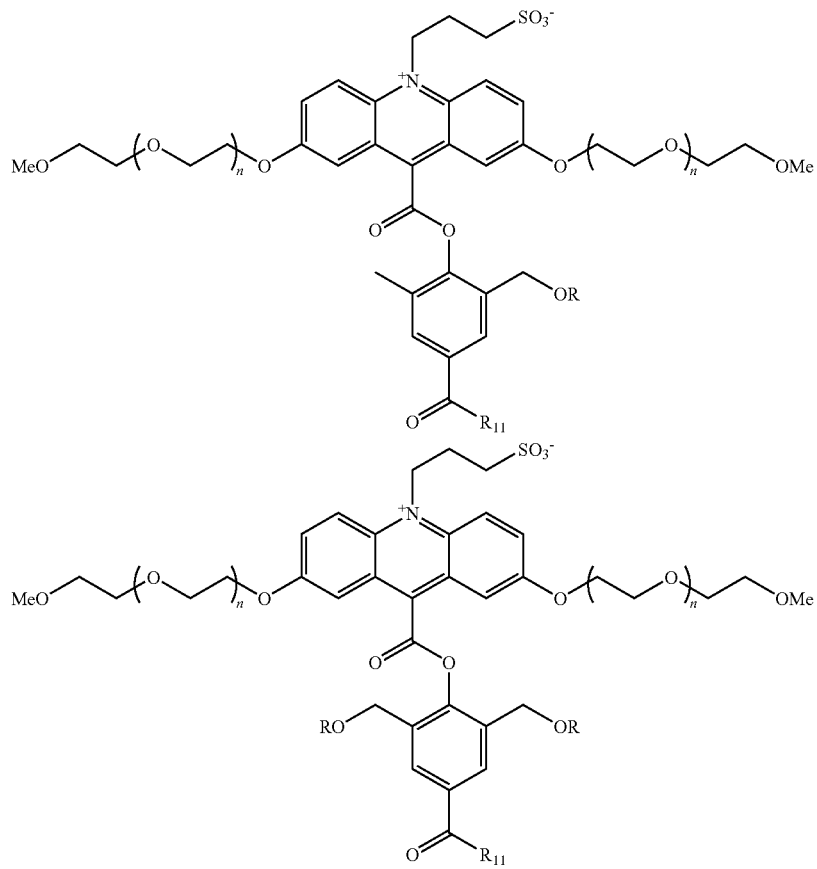

where R is selected from -Me, —CH$_2$CH$_2$OMe, —CHMe$_2$-(CH$_2$CH$_2$O)$_n$CH$_2$CH$_2$OMe, and —CH[CH$_2$O(CH$_2$CH$_2$O)$_n$CH$_2$CH$_2$OMe]$_2$, where n=1-5 and R$_{11}$ is as described previously.

The hydrolytically stable, fast light emitting acridinium compounds of the invention are useful as labels in assays for the determination or quatitation of analytes. Acridinium compounds are used extensively in immunoassays and nucleic acid assays. Analytes that are typically measured in such assays are often substances of some clinical relevance and can span a wide range of molecules from large macromolecules such as proteins, nucleic acids, viruses bacteria, etc. to small molecules such as ethanol, vitamins, steroids, hormones, therapeutic drugs, etc. A 'sandwich' immunoassay typically involves the detection of a large molecule, also referred to as macromolecular analyte, using two binding molecules such as antibodies. One antibody is immobilized or attached to a solid phase such as a particle, bead, membrane, microtiter plate or any other solid surface. Methods for the attachment of binding molecules such as antibodies to solid phases are well known in the art. For example, an antibody can be covalently attached to a particle containing amines on its surface by using a cross-linking molecule such as glutaraldehyde. The attachment may also be non-covalent and may involve simple adsorption of the binding molecule to the surface of the solid phase, such as polystyrene beads and microtiter plate. The second antibody is often covalently attached with a chemiluminescent or fluorescent molecule often referred to as a label. Labeling of binding molecules such as antibodies and other binding proteins are also well known in the art and are commonly called conjugation reactions and the labeled antibody is often called a conjugate. Typically, an amine-reactive moiety on the label reacts with an amine on the antibody to form an amide linkage. Other linkages such as thioether, ester, carbamate, and the like, between the antibody and the label are also well known. In the assay, the two antibodies bind to different regions of the macromolecular analyte. The macromolecular analyte can be, for example, proteins, nucleic acids, oligosaccharides, antibodies, antibody fragments, cells, viruses, receptors, or synthetic polymers. The binding molecules can be antibodies, antibody fragments, nucleic acids, peptides, binding proteins or synthetic binding polymers. For example the folate binding protein ("FBP") binds the analyte folate. Synthetic binding molecules that can bind a variety of analytes have also been disclosed by Mossbach et al. *Biotechnology* vol. 14, pp. 163-170 (1995).

When the solid phase with the immobilized antibody and the labeled antibody is mixed with a sample containing the analyte, a binding complex is formed between the analyte and the two antibodies. This type of assay is often called a heterogenous assay because of the involvement of a solid phase. The chemiluminescent or fluorescent signal associated with the binding complex can then be measured and the presence or absence of the analyte can be inferred. Usually, the binding complex is separated from the rest of the binding reaction components such as excess, labeled antibody prior to signal generation. For example if the binding complex is associated with a magnetic bead, a magnet can be used to separate the binding complex associated with the bead from bulk solution. By using a series of 'standards', that is, known concentrations of the analyte, a 'dose-response' curve can be generated using the two antibodies. Thus, the dose-response curve correlates a certain amount of measured signal with a specific concentration of analyte. In a sandwich assay, as the concentration of the analyte increases, the amount of signal also increases. The concentration of the analyte in an unknown sample can then be calculated by comparing the signal generated by an unknown sample containing the macromolecular analyte, with the dose-response curve.

In a similar vein, the two binding components can also be nucleic acids that bind or hybridize to different regions of a nucleic acid analyte. The concentration of the nucleic acid analyte can then be deduced in a similar manner.

Another class of immunoassays for small molecule analytes such as steroids, vitamins, hormones, therapeutic drugs or small peptides employs an assay format that is commonly referred to as a competitive assay. Typically, in a competitive assay, a conjugate is made of the analyte of interest and a chemiluminescent or fluorescent label by covalently linking the two molecules. The small molecule analyte can be used as such or its structure can be altered prior to conjugation to the label. The analyte with the altered structure is called an analog. It is often necessary to use a structural analog of the analyte to permit the chemistry for linking the label with the analyte. Sometimes a structural analog of an analyte is used to attenuate or enhance its binding to a binding molecule such an antibody. Such techniques are well known in the art. The antibody or a binding protein to the analyte of interest is often immobilized on a solid phase either directly or through a secondary binding interaction such as the biotin-avidin system.

The concentration of the analyte in a sample can be deduced in a competitive assay by allowing the analyte-containing sample and the analyte-label conjugate to compete for a limited amount of solid phase-immobilized binding molecule. As the concentration of analyte in a sample increases, the amount of analyte-label conjugate captured by the binding molecule on the solid phase decreases. By employing a series of 'standards', that is, known concentrations of the analyte, a dose-response curve can be constructed where the signal from the analyte-label conjugate captured by the binding molecule on the solid phase is inversely correlated with the concentration of analyte. Once a dose-response curve has been devised in this manner, the concentration of the same analyte in an unknown sample can be deduced by comparing the signal obtained from the unknown sample with the signal in the dose-response curve.

Another format of the competitive assay for small molecules analytes involves the use of a solid phase that is immobilized with the analyte of interest or an analyte analog and an antibody or a binding protein specific for the analyte that is conjugated with a chemiluminescent or fluorescent label. In this format, the antibody-label conjugate is captured onto the solid phase through the binding interaction with the analyte or the analyte analog on the solid phase. The analyte of interest present in a sample then "competitively" binds to the antibody-label conjugate and thus inhibits or replaces the interaction of the antibody-label conjugate with the solid phase. In this fashion, the amount of signal generated from the antibody-label conjugate captured on the solid phase is correlated to the amount of the analyte in sample.

Acridinium esters are extremely useful chemiluminescent labels especially in automated immunochemistry instruments such as Bayer's ADVIA:Centaur™ and ACS: 180™ which use the hydrolytically stable acridinium esters DMAE and NSP-DMAE. Both these instruments have high throughput by which is meant they are capable of running a large number immunoassay tests, 240 and 180 tests respectively, every hour. The reagents derived from NSP-DMAE typically emit light over a period of five seconds when their chemiluminescence is triggered with the addition of 100 mM nitric acid containing 0.5% hydrogen peroxide followed by 0.25 N sodium hydroxide containing a surfactant. The fast light emitting and stable acridinium esters of the invention can be used in automated immunochemistry instruments such as the ADVIA:Centaur™ to increase their throughput. By "increased throughput" is meant increasing the number of tests that can be run in a given amount of time as compared to the otherwise identical test employing the acridinium esters DMAE and NSP-DMAE.

One key factor that can affect the throughput of an automated immunochemistry instrument using chemiluminescent acridinium esters is the light measuring time. In the ADVIA:Centaur™, the light measuring time is four seconds for the collection of all the light emitted by the acridinium ester reagents. The fast light emitting acridinium esters of the invention permit light measuring times to be reduced from 4 seconds to 1-2 seconds when their chemiluminescence is triggered using the triggering reagents 100 mM nitric acid containing 0.5% hydrogen peroxide and 0.25 N sodium hydroxide containing a surfactant.

More specifically, we have found that the placement of heteroatoms, such as oxygen, having lone pairs of electrons on the methylene carbons at C-2' and/or C-6' of the phenol leaving group leads to faster rate emission from the corresponding acridinium esters when compared to those acridinium esters lacking these substituents when their chemiluminescence is triggered using the reagents 100 mM nitric acid containing 0.5% hydrogen peroxide and 0.25 N sodium hydroxide containing a surfactant. The C-2' and C-6' methylene carbons on the phenol are equivalent due to rotation of the phenoxy group. When the acridinium ester contains one substituent or functional group at one of these carbons, it is referred to as a substituent on the C-2' methyl group.

In Table 1, light emission from various acridinium esters of the present invention are summarized. The chemical structures of the various acridinium compounds listed in Table 1 are shown below. The acridinium compounds listed in Table 1 were synthesized using organic chemistry techniques well known to practitioners in the field. The acridinium esters NSP-DMAE and NSP-2,7-(OMHEG)$_2$-DMAE (US 2005/0221390A1), do not have any heteroatoms on the C-2' or C-6' methyl groups on the phenol, were used as reference compounds (entries 1 and 2 in Table 1). Whereas NSP-DMAE does not have any substituents on the acridinium ring, NSP-2,7-(OMHEG)$_2$-DMAE has two hydrophilic O-methoxyhexa(ethylene)glycol moieties (OMHEG) on the C-2 and C-7 methyl groups of the acridinium ring. Synthesis details pertaining to the compounds in Table 1 can be found in the Examples section. Light emission from each compound was triggered by the addition of two reagents. The first reagent comprised 0.5% hydrogen peroxide in 100 mM nitric acid while the second reagent contained a surfactant in 0.25 N sodium hydroxide. Light was measured using a luminometer equipped with a photo-multiplier tube as the detector. The amount of light emitted from each compound was measured as a function of measuring time, which was varied. The amount of light emitted at each measuring time was reported as Relative Light Units (RLUs) by the luminometer. The amount of light emitted as RLUs was found to be maximal at a measuring time of 10 s for the slowest acridinium esters and was assigned to be 100% at this time point for all the acridinium esters. Light emission at shorter measuring times are represented as fractions of this number and are also expressed as percentages in Table 1. Other details pertaining to these measurements can be found in the Examples section.

TABLE 1

| | | % RLU at measuring time | | | | |
|---|---|---|---|---|---|---|
| Entry | Compound | 0.5 s | 1.0 s | 2.0 s | 5.0 s | 10 s |
| 1 | NSP-DMAE | 4.1 | 22 | 47 | 82 | 100 |
| 2 | NSP-2,7-(OMHEG)$_2$-DMAE | 3 | 22 | 50 | 85 | 100 |
| 3 | NSP-2'-(CH$_2$OMe)'-Me-AE | 15 | 69 | 92 | 98 | 100 |
| 4 | NSP-2'-(CH$_2$OCH$_2$CH$_2$OMe)-6'-Me-AE | 15 | 80 | 96 | 98 | 100 |
| 5 | NSP-2'-(CH$_2$O[CH$_2$CH$_2$O]$_2$CH$_2$CH$_2$OMe)-6'-Me-AE | 21 | 81 | 92 | 98 | 100 |
| 6 | NSP-2',6'-(CH$_2$OCH$_2$CH$_2$OMe)$_2$Me-AE | 86 | 98 | 99 | 100 | 100 |
| 7 | NSP-2'-(CH$_2$OCH[Me]2)-6'-Me-AE | 27 | 83 | 93 | 99 | 100 |
| 8 | NSP-2,7-(OMHEG)$_2$-2'-(CH$_2$O[CH$_2$CH$_2$O]$_2$CH$_2$CH$_2$OMe)-6'-Me-AE | 39 | 90 | 94 | 99 | 100 |
| 9 | NSP-2'-(CH$_2$CH[OMe]Me)-6'-Me-AE | 3 | 21 | 49 | 84 | 100 |
| 10 | NSP-2'-(CH$_2$CH$_2$OMe)-6'-Me-AE | 5 | 35 | 68 | 92 | 100 |

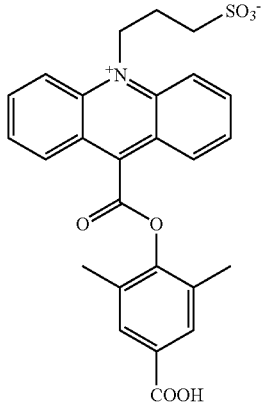

NSP-DMAE

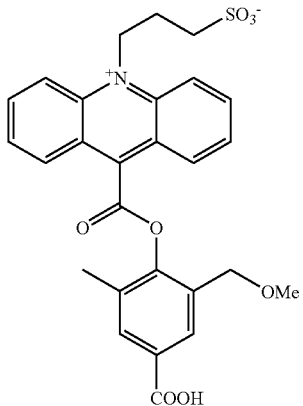

NSP-2'-(CH$_2$OMe)-6'-Me-AE

TABLE 1-continued
| | | % RLU at measuring time | | | | |
|---|---|---|---|---|---|---|
| Entry | Compound | 0.5 s | 1.0 s | 2.0 s | 5.0 s | 10 s |
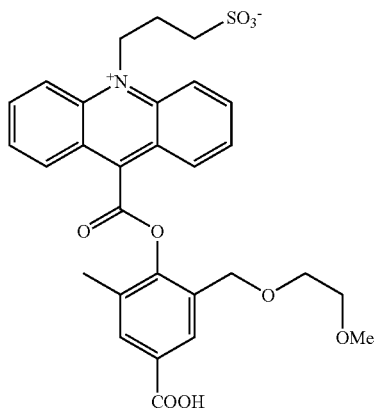
NSP-2'-(CH$_2$OCH$_2$CH$_2$OMe)-6-Me-Ae
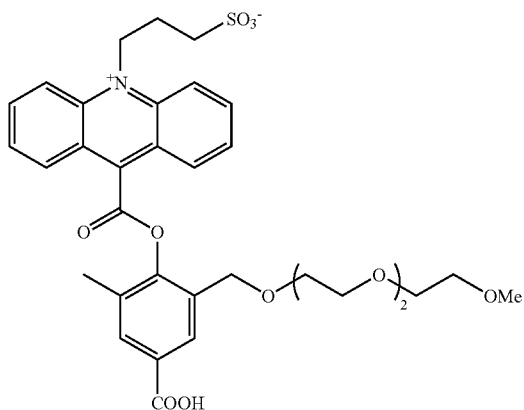
NSP-2'-(CH$_2$O[CH$_2$CH$_2$O]$_2$CH$_2$CH$_2$OMe)-6'-Me-Ae
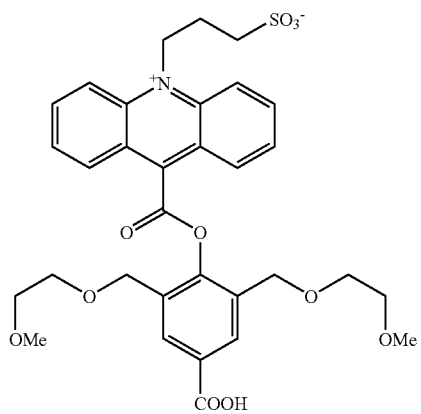
NSP-2',6'-(CH$_2$OCH$_2$CH$_2$OMe)$_2$-AE TABLE 1-continued
| | | % RLU at measuring time | | | | |
|---|---|---|---|---|---|---|
| Entry | Compound | 0.5 s | 1.0 s | 2.0 s | 5.0 s | 10 s |
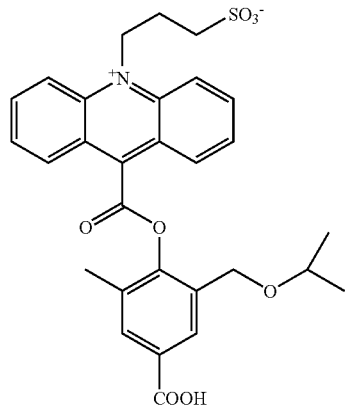
NSP-2'-(CH₂OCH[Me]₂)-6'-Me-AE
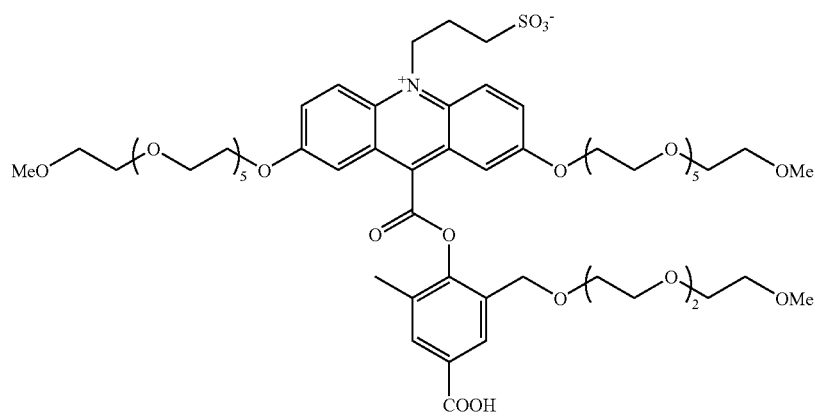
NSP-2,7-(OMHEG)₂-2'-(CH₂O[CH₂CH₂O]₂CH₂CH₂OMe)-6'-Me-AE
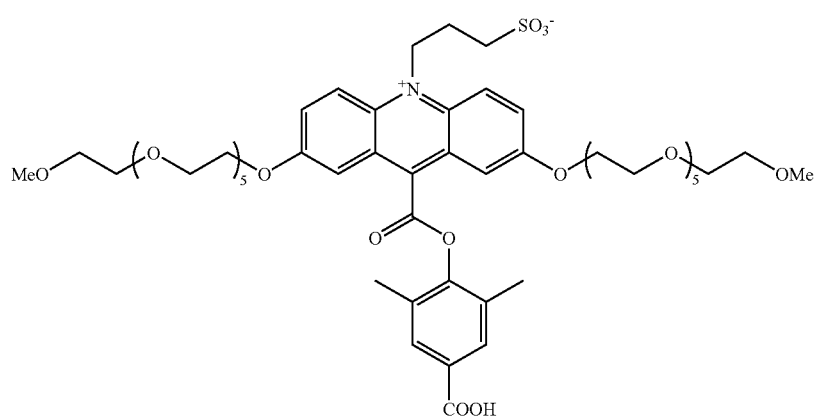
NSP-2,7(OMHEG)₂-DMAE TABLE 1-continued

| | | % RLU at measuring time | | | | |
|---|---|---|---|---|---|---|
| Entry | Compound | 0.5 s | 1.0 s | 2.0 s | 5.0 s | 10 s |

NSP-2'-(CH₂CH₂OMe)-6'-Me-AE

NSP-2'-(CH₂CHOMe[Me])-6'-Me-AE

From inspection of the data in Table 1, it can be deduced that acridinium esters containing the ether, —OR substituents on the C-2' and/or C-6' methyl groups show accelerated light emission, where R is an alkyl group, with or without additional heteroatoms and with or without branching. This point is most clearly evident by considering the amount of light that is emitted at the 2 second measuring time for all the compounds. For NSP-DMAE (entry 1), which lacks the —OR substituents at the C-2' and C-6' methyl groups, 47% of the total light is emitted in 2 seconds. Similarly for NSP-2,7-(OMHEG)₂-DMAE, (entry 2), only 50% of the total light is emitted in 2 seconds. In sharp contrast, all the other compounds listed in Table 1 from entries 3-8, emit >90% of their light within 2 seconds and they all contain heteroatoms, in the form of ether —OR groups, on the C-2' and/or C-6' methylene carbon atoms. For example, the compounds NSP-2'-(CH₂OMe)-6'-Me-AE and NSP-2'-(CH₂OCH₂CH₂OMe)-6'-Me-AE (entries 3 and 4 respectively), emit 92% and 96% of their light respectively in 2 seconds. The compound NSP-2'-(CH₂O[CH₂CH₂O]₂CH₂CH₂OMe)-6'-Me-AE, which has a even longer alkyl chain attached to the C-2' methylene, also shows fast light emission with 92% of its light emitted in 2 seconds (entry 5, table 1). Thus, the length of the alkyl group R on the —OR substituent has no effect on the rate acceleration, as illustrated for entries 3, 4 and 5. In addition, branching at R also does not impact fast light emission. For example the compound NSP-2'-(CH₂OCH[Me]₂)-6'-Me-AE, (entry 7, table 1) which has additional branching at R also shows fast light emission with 93% of its light being emitted in 2 seconds. The compound NSP-2',6'-(CH₂OCH₂CH₂OMe)₂ Me-AE (entry 6, Table 1) has two heteroatom substituents on the C-2' and C-6' methyl carbons and shows even faster light emission than the mono-substituted acridinium esters which contain only one heteroatam on the C-2' methylene carbon atom. This is most evident when considering the amount of light that is emitted for each compound at the very short 1.0 second measuring time. This compound emits 98% of its light after only one second. All the other fast light emitting acridinium esters containing one heteroatom on the C-2' methylene carbon (entries 3-6, 8) emit 69-90% of their light in one second. The two compounds lacking any heteroatoms on the C-2'methyl carbon, NSP-DMAE and NSP-2,7-(OMHEG)₂-DMAE (entries 1 and 2) emit only 22% of their light after one second. The results of Table 1 also show that functional groups on the acridinium ring do not inhibit the ability of an —OR group on the C-2' methyl carbon from accelerating light emission. Thus, the compound NSP-2,7-(OMHEG)₂-2'-(CH₂O[CH₂CH₂O]₂CH₂CH₂OMe)-6'-Me-AE (entry 8) emits 94% of its light in 2 seconds when the analogous compound NSP-2,7-(OMHEG)₂-DMAE with the same functional groups on the acridinium ring but lacking the heteroatom emits only 50% of its light in the same time. Finally, entries 9 and 10 illustrate that to obtain fast light emission, the heteroatom —OR group must be situated directly on the C-2' methylene carbon. For the two compounds NSP-2'-(CH$_2$CH[OMe]Me)-6'-Me-AE (entry 9) and NSP-2'-(CH$_2$CH$_2$OMe)-6'-Me-AE (entry 10) which have additional intervening carbon atoms between the C-2' methylene carbon and the —OR group, light emission is much slower. These two compounds emit only 49% and 68% of their light respectively after 2 seconds. Thus, the functional group —CH$_2$OR at the C-2' methylene carbon is ineffective in accelerating light emission from acridinium esters containing this functional group while the —OR group is effective. The —OR group is not unique and other heteroatoms with lone pair(s) of electrons in functional groups such as thioether (—SR) and amine (—NR$_2$) can also be expected to accelerate light emission from acridinium esters containing these functional groups at the C-2' and/or C-6' methyl carbon atoms. The R group, as shown above does not have an impact on light emission and therefore can be any alkyl or aryl group or some combination of these with or without additional functional groups located on the R group.

The fast light emitting acridinium esters of the present invention also show fast light emission when they are conjugated to macromolecules such as proteins or small molecules such as steroids. In Table 2 light emission from acridinium ester conjugates of an anti-TSH monoclonal antibody (anti-TSH Mab) and cortisol conjugates are summarized. These measurements were made as described earlier for the data in Table 1 only here, light emission measured at 5 seconds was observed to be maximal for the slowest acridinium ester conjugates and was assigned to be 100% for all conjugates. The analytes TSH (Thyroid Stimulating Hormone) and the steroid cortisol are commonly measured by immunochemical techniques. The structures of the acridinium esters and the conjugates are illustrated in the drawing below Table 2. Synthesis details pertaining to the conjugates are described in detail in the Examples section.

TABLE 2

| | | % RLU at measuring time | | | |
|---|---|---|---|---|---|
| Entry | Conjugate | 0.5 s | 1.0 s | 2.0 s | 5.0 s |
| 1 | NSP-DMAE-anti-TSH Mab | 21 | 69 | 87 | 100 |
| 2 | NSP-DMAE-HEG-glutarate-anti-TSH Mab | 8 | 52 | 85 | 100 |
| 3 | NSP-2,7-(OMHEG)$_2$-DMAE-AC-anti-TSH Mab | 15 | 62 | 89 | 100 |
| 4 | NSP-2'-(CH$_2$OCH$_2$CH$_2$OMe)-6'-Me-AE-anti-TSH Mab | 68 | 94 | 98 | 100 |
| 5 | NSP-2'-(CH$_2$OCHMe$_2$)-6'-Me-AE-anti-TSH Mab | 66 | 98 | 98 | 100 |
| 6 | NSP-2,7-(OMHEG)$_2$-2'-(CH$_2$OMe)-6'-Me-AE-AC-anti-TSH Mab | 66 | 98 | 98 | 100 |
| 7 | NSP-2'-(CH$_2$OMe)-6'-Me-AE-HEG-glutarate-anti-TSH Mab | 48 | 94 | 97 | 100 |
| 8 | NSP-2'-(CH$_2$OCH$_2$CH$_2$OMe)-6'-Me-AE-HEG-glutarate-anti-TSH Mab | 52 | 90 | 97 | 100 |
| 9 | NSP-DMAE-HEG-Cortisol | 5 | 38 | 78 | 100 |
| 10 | NSP-2'-(CH$_2$OCH$_2$CH$_2$OMe)-6'-Me-AE-HEG-Cortisol | 46 | 98 | 98 | 100 |
| 11 | NSP-2'-(CH$_2$OMe)-6'-Me-AE-HEG-Cortisol | 36 | 96 | 100 | 100 |

Chemiluminescence was measured on a Magic Lite Analyzer Luminometer (MLA1, Bayer Diagnostics). For the measurements, samples of the various compounds were prepared in 10 mM phosphate pH 8 containing 150 mM NaCl, 0.05% BSA and 0.01% sodium azide.

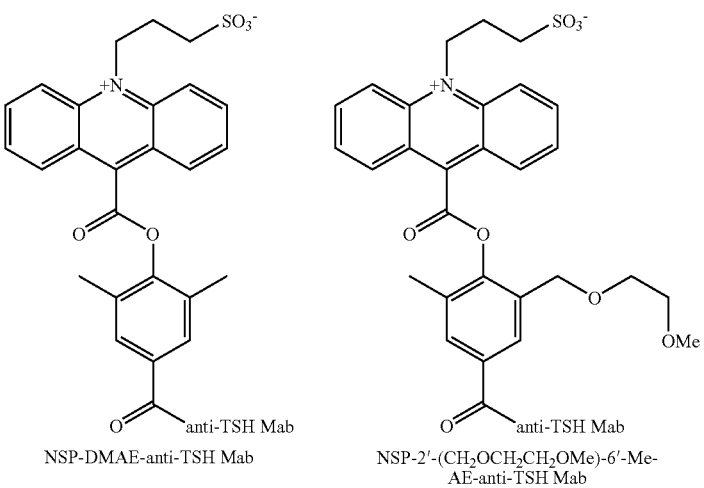

NSP-DMAE-anti-TSH Mab

NSP-2'-(CH$_2$OCH$_2$CH$_2$OMe)-6'-Me-AE-anti-TSH Mab

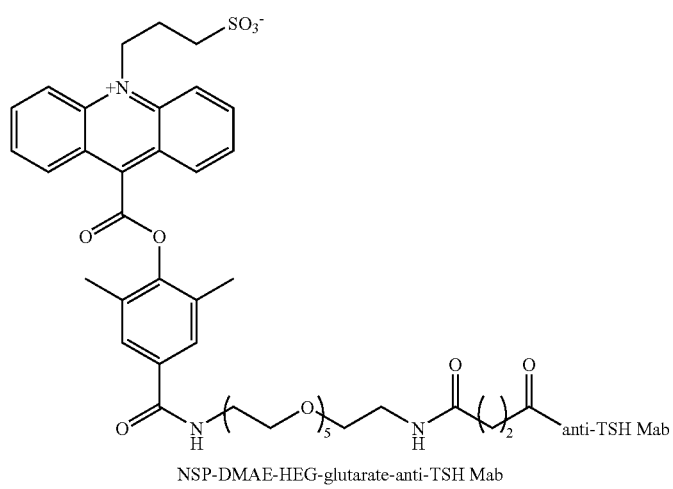
NSP-DMAE-HEG-glutarate-anti-TSH Mab
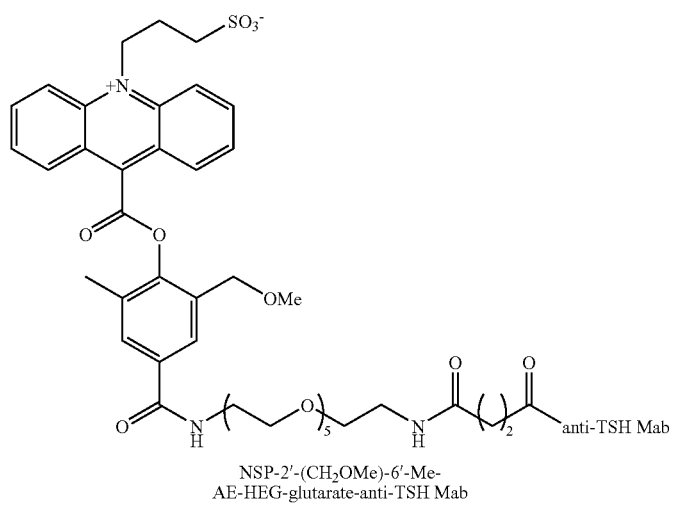
NSP-2′-(CH₂OMe)-6′-Me-
AE-HEG-glutarate-anti-TSH Mab
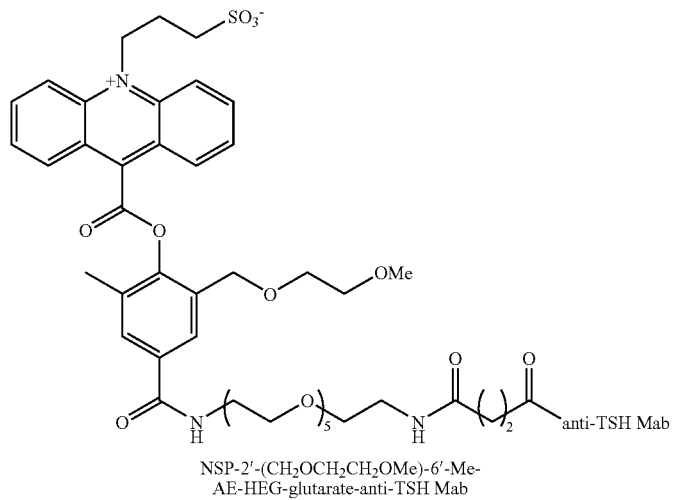
NSP-2′-(CH₂OCH₂CH₂OMe)-6′-Me-
AE-HEG-glutarate-anti-TSH Mab

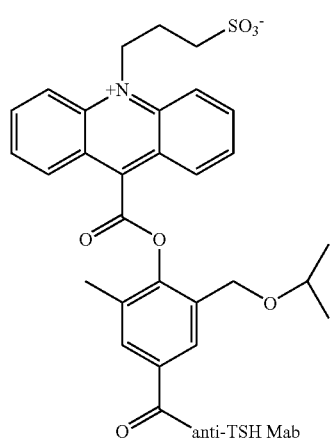
NSP-2'-(CH₂OCHMe₂)-6'-Me-
AE-anti-TSH Mab
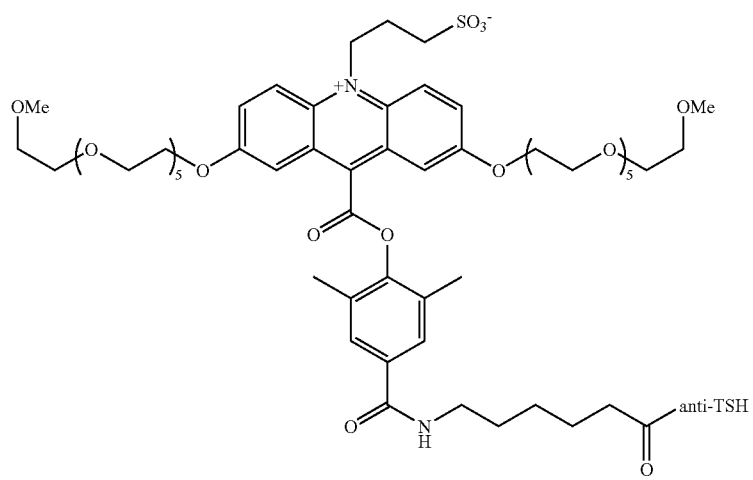
NSP-2,7-(OMHEG)₂-DMAE-AC-anti-TSH Mab
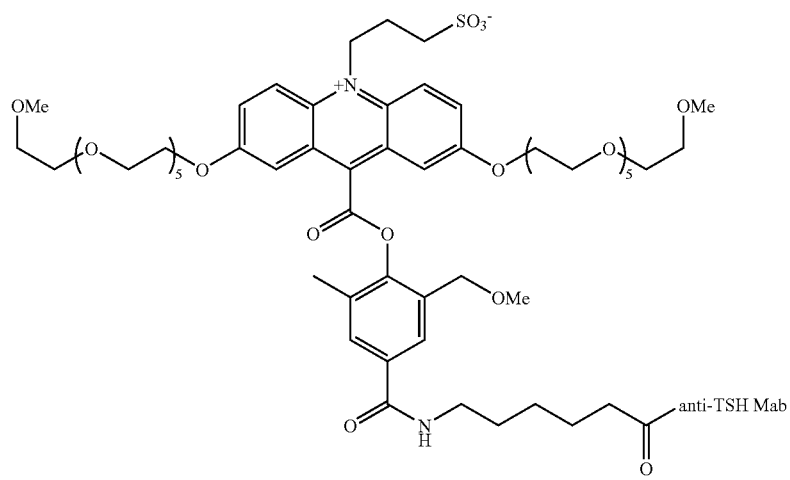
NSP-2,7-(OMHEG)₂-2'-(CH₂OMe)-6'-Me-
AE-AC-anti-TSH Mab
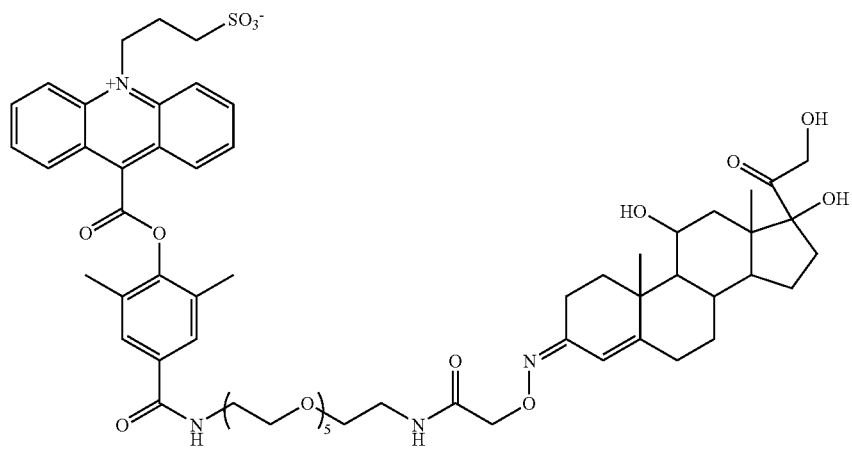
NSP-DMAE-HEG-Cortisol

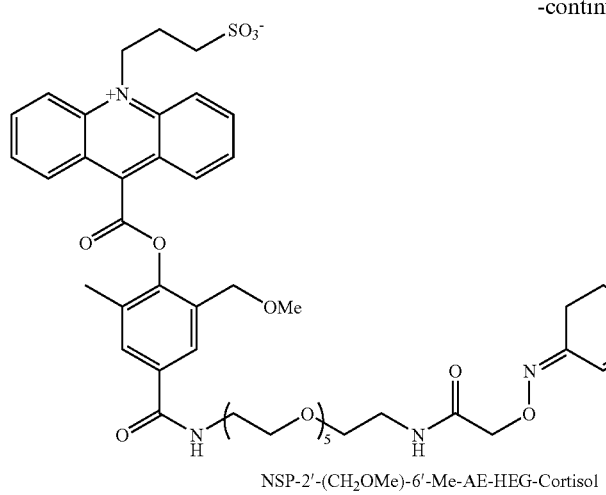

NSP-2'-(CH$_2$OMe)-6'-Me-AE-HEG-Cortisol

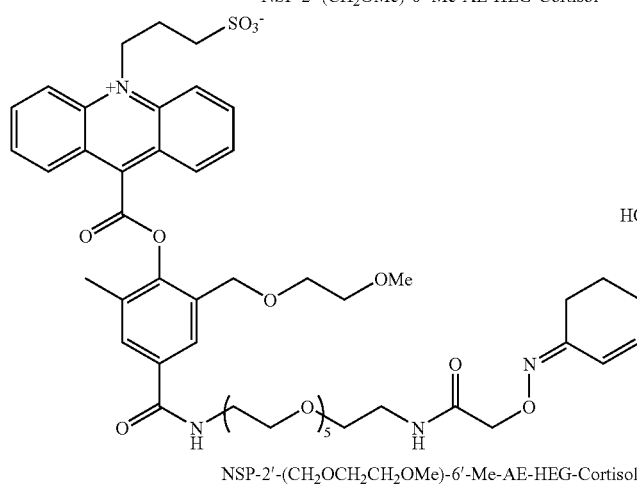

NSP-2'-(CH$_2$OCH$_2$CH$_2$OMe)-6'-Me-AE-HEG-Cortisol

The data in Table 2 show that acridinium esters containing heteroatoms on the C-2' methylene carbon show fast light emission even when they are conjugated to other molecules. Acridinium esters lacking heteroatoms at the C-2' methyl carbon, show slower light emission. For example, anti-TSH Mab conjugates derived from NSP-DMAE (entry 1, Table 2) and NSP-DMAE-HEG-glutarate (entry 2, Table 2) emit 69% and 52% of their light in one second respectively. Similarly, the anti-TSH Mab conjugate of the acridinium ester NSP-2,7-(OMHEG)$_2$-DMAE-AC, which contains -OMHEG moieties at C-2 and C-7 on the acridinium ring but, no heteroatoms on the C-2' methyl carbon emits 62% of its light in one second (entry 3, Table 2). In contrast, anti-TSH Mab conjugates derived from compounds containing heteroatoms on the C-2' methylene carbon all show fast light emission (entries 4-8, Table 2). Thus, the conjugate of NSP-2'-(CH$_2$OCH$_2$CH$_2$OMe)-6'-Me-AE (entry 4) emits 94% of its light in one second. Similarly the conjugates of NSP-2'-(CH$_2$OCHMe$_2$)-6'-Me-AE (entry 5), NSP-2'-(CH$_2$OMe)-6'-Me-AE-HEG-glutarate (entry 7) and NSP-2'-(CH$_2$OCH$_2$CH$_2$OMe)-6'-Me-AE-HEG-glutarate (entry 8) emit 94%, 98% and 90% of their light respectively in one second. The conjugate of NSP-2,7-(OMHEG)$_2$-2'-(CH$_2$OMe)-6'-Me-AE-AC, (entry 6) which besides containing OMHEG functional groups on the acridinium ring also contains a heteroatom at the C-2' methylene carbon also shows fast light emission with 98% of its light emitted in one second.

The cortisol conjugates of the acridinium esters show similar trends. The conjugate NSP-DMAE-HEG-Cortisol (see U.S. Pat. No. 6,664,043 B2 for similar structures and synthesis of NSP-DMAE-HEG), which does not contain any heteroatom at C-2' methyl carbon emits only 38% of its light in one second (entry 9). In contrast, both the conjugates NSP-2'-(CH$_2$OCH$_2$CH$_2$OMe)-6'-Me-AE-HEG-Cortisol and NSP-2'-(CH$_2$OMe)-6'-Me-AE-HEG-Cortisol (entries 10 and 11) which contain oxygen on the C-2' methylene carbon emit 98% and 96% of their light in one second respectively.

In addition to showing fast light emission, the acridinium esters of the present invention also show good stability. By "stability," is meant a minimal loss of RLUs (i.e., less than 25%, preferably less than 20%, and more preferably, less than 15%) when the compounds or conjugates are stored in an aqueous solution typically, in the pH range of 7-8, which is within the physiological pH. From a mechanistic viewpoint, hydrolysis of the phenolic ester is the main pathway by which chemiluminescent acridinium esters become non-chemiluminescent. Stable conjugates ensure long shelf life for acridinium ester reagents and also ensure that assay performance does not vary greatly over a given period of time. The stability of various acridinium ester conjugates of the present invention are listed in Tables 3 and 4. Aqueous solutions of the conjugates were stored at room temperature in an aqueous buffer at pH 7.7 and RLUs were recorded periodically. The RLUs that were measured at the initial time point, also referred to as day 0, were assigned a value of 100%. The RLUs that were measured at other time points, are expressed as percentages of this number. Other details pertaining to these measurements can be found in the Examples section.

TABLE 3

| | | % RLU | |
|---|---|---|---|
| time (days) | NSP-DMAE-anti-TSH Mab | NSP-2'-(CH$_2$OCH$_2$CH$_2$OMe)-6'-Me-AE-anti-TSH Mab | NSP-2'-(CH$_2$OCHMe$_2$)-6'-Me-AE-anti-TSH Mab |
| 0 | 100 | 100 | 100 |
| 7 | 95 | 95 | 97 |
| 13 | 97 | 93 | 94 |
| 20 | 93 | 87 | 90 |
| 27 | 92 | 82 | 93 |

TABLE 4

| | % RLU | |
|---|---|---|
| time (days) | NSP-DMAE-HEG-Cortisol | NSP-2'-(CH$_2$OMe)-6'-Me-AE-HEG-Cortisol |
| 0 | 100 | 100 |
| 1 | 101 | 106 |
| 2 | 99 | 104 |
| 6 | 102 | 105 |
| 9 | 105 | 108 |
| 14 | 108 | 102 |
| 23 | 98 | 91 |
| 27 | 104 | 95 |

As can be seen from Tables 3 and 4, the anti-TSH Mab and the cortisol conjugates of the fast light emitting acridinium esters of the present invention are quite stable to RLU change. Even after 27 days at room temperature, the anti-TSH Mab conjugates of NSP-2'-(CH$_2$OCH$_2$CH$_2$OMe)-6'-Me-AE and NSP-2'-(CH$_2$OCHMe$_2$)-6'-Me-AE retain 82% and 93% of their initial chemiluminescent signal respectively when compared to NSP-DMAE which retains 92% of its initial chemiluminescence. The cortisol conjugates of NSP-DMAE and the fast light emitting NSP-2'-(CH$_2$OMe)-6'-Me-AE show retention of 104% and 95% of their initial RLUs respectively after storage at room temperature for 27 days.

In accordance with the foregoing, an assay for the detection or quantification of an analyte comprises, according to one embodiment of the invention, the following steps:

(a) providing a conjugate comprising: (i) a binding molecule specific for an analyte; and (ii) any of the inventive hydrolytically stable, fast light emitting acridinium esters having heteroatoms, preferably oxygen, on the C-2' methyl group, as defined herein;

(b) providing a solid support having immobilized thereon a second binding molecule specific for said analyte;

(c) mixing the conjugate, the solid phase and a sample suspected of containing the analyte to form a binding complex;

(d) separating the binding complex captured on the solid support;

(e) triggering chemiluminescence of the binding complex from step (d) by adding chemiluminescence triggering reagents;

(f) measuring the amount of light emission with a luminometer; and (g) detecting the presence or calculating the concentration of the analyte by comparing the amount of light emitted from the reaction mixture with a standard dose response curve which relates the amount of light emitted to a known concentration of the analyte.

In another embodiment, an assay for the detection or quantification of an analyte is provided comprising the steps of:

(a) providing a conjugate of an analyte with any of the inventive hydrolytically stable, fast light emitting acridinium esters having heteroatoms, preferably oxygen, on the C-2' methyl group, as defined herein;

(b) providing a solid support immobilized with a binding molecule specific for the analyte;

(c) mixing the conjugate, solid support and a sample suspected of containing the analyte to form a binding complex;

(d) separating the binding complex captured on the solid support;

(e) triggering the chemiluminescence of the binding complex from step (d) by adding chemiluminescence triggering reagents;

(f) measuring the amount of light with an luminometer; and (g) detecting the presence or calculating the concentration of the analyte by comparing the amount of light emitted from the reaction mixture with a standard dose response curve which relates the amount of light emitted to a known concentration of the analyte.

Macromolecular analytes can be proteins, nucleic acids, oligosaccharides, antibodies, antibody fragments, cells, viruses, synthetic polymers, and the like.

Small molecule analytes can be steroids, vitamins, hormones, therapeutic drugs, small peptides, and the like.

The binding molecules in the assays can be an antibody, an antibody fragment, a binding protein, a nucleic acid, a peptide, a receptor or a synthetic binding molecule.

Example 1

Synthesis of NSP-2'-(CH$_2$OCH$_2$CH$_2$OMe)-6'-Me-AE-NHS, NSP-2'-(CH$_2$OCH$_2$CH$_2$OMe)-6'-Me-AE-HEG, NSP-2'-(CH$_2$OCH$_2$CH$_2$OMe)-6'-Me-AE HEG-glutarate NHS ester and NSP-2'-(CH$_2$OCH$_2$CH$_2$OMe)-6'-Me-AE HEG-cortisol a) Synthesis of methyl 3,5-dimethyl-4-hydroxybenzoate A solution of 3,5-dimethyl-4-hydroxybenzoic acid (2 g, 0.012 mol) in anhydrous methanol (60 mL) was cooled in an ice-bath and thionyl chloride (5 mL) was added drop wise to this solution. The reaction was stirred in the ice-bath for one hour and was then warmed to room temperature and stirred for 16 hours. Solid sodium bicarbonate was then added to neutralize the acid and then the mixture was evaporated to dryness by rotary evaporation. The residue was partitioned between ethyl acetate and water (100 mL each). The ethyl acetate layer was separated and washed once with brine. It was then dried over anhydrous magnesium sulfate, filtered and evaporated to dryness. Yield=2.146 g, white powder.

b) Synthesis of methyl 4-acetoxy-3,5-dimethylbenzoate

A solution of methyl 3,5-dimethyl-4-hydroxybenzoate (2.146 g) in pyridine (20 mL) was cooled in an ice-bath under a nitrogen atmosphere. Acetic anhydride (5 mL) was added drop wise and after 30 minutes at 0° C., the reaction was warmed to room temperature and stirred for 2-3 hours. The solvent was then removed under reduced pressure and the crude product was dissolved in ethyl acetate (50 mL). This solution was washed with 1 N HCl, water and brine. It was then dried over anhydrous magnesium sulfate, filtered and evaporated to dryness. Yield=2.4 g, white powder.

c) Synthesis of methyl 4-acetoxy-3-bromomethyl-5-methylbenzoate

A solution of methyl 4-acetoxy-3,5-dimethylbenzoate (2.4 g) in carbon tetrachloride (35 mL) was treated with AIBN (azobisisobutrylnitrile, 0.177 g, 0.1 equivalent) and NBS (N-bromosuccinimide, 2.117 g, 1.1 equivalents). The reaction was heated at reflux under a nitrogen atmosphere for 6 h. The reaction was cooled to room temperature and diluted with chloroform (30 mL). This solution was washed with water (4×50 mL) and then dried over anhydrous magnesium sulfate, filtered and evaporated to dryness. An off-white, waxy solid was recovered. Yield=4.63 g. The crude bromide was used as such for the following reaction.

d) Synthesis of methyl 3-($CH_2OCH_2CH_2OMe$)-4-hydroxy-5-methylbenzoate

A suspension of crude methyl 4-acetoxy-3-bromomethyl-5-methylbenzoate (~0.5 g) was heated in 5 mL of 2-methoxyethanol along with sodium bicarbonate (0.765 g, ~5 equivalents) at 90-95° C. under a nitrogen atmosphere. After 2 hours, TLC analysis indicated complete conversion. The reaction was cooled to room temperature and evaporated to dryness. The residue was partitioned between ethyl acetate (40 mL) and water (40 mL). The ethyl acetate layer was separated and dried over anhydrous magnesium sulfate. It was then filtered and evaporated to dryness to afford 338 mg of a viscous oil which was purified by preparative TLC on silica using 25% ethyl acetate/hexanes. Purified Yield=83 mg (viscous oil).

e) Synthesis of 2'-($CH_2OCH_2CH_2OMe$)-4'-methoxycarbonylphenyl-6'-Me-acridine 9-carboxylate A suspension of acridine-9-carboxylic acid (66 mg, 0.6 mmol) in pyridine (5 mL) was treated with p-toluene sulfonyl chloride (115 mg, 0.6 mmol). After stirring vigorously for 10 minutes, a solution of methyl 3-($CH_2OCH_2CH_2OMe$)-4-hydroxy-5-methylbenzoate (76 mg, 0.3 mmol) in pyridine (1 mL) was added and the reaction was stirred at room temperature under a nitrogen atmosphere for 4 days. The solvent was then removed under reduced pressure and the residue was dissolved in chloroform (40 mL). This solution was washed repeatedly with saturated aqueous sodium bicarbonate until the bicarbonate layer was clear. The chloroform layer was then washed once with 1 N HCl and brine. It was then dried over anhydrous magnesium sulfate, filtered and evaporated to dryness. The crude product (128 mg) was purified by preparative TLC on silica using 10% ethyl acetate/chloroform. Purified Yield=94 mg (70%).

f) Synthesis of NSP-2'-($CH_2OCH_2CH_2OMe$)-6'-Me-AE

A mixture of 2'-($CH_2OCH_2CH_2OMe$)-4'-methoxycarbonylphenyl-6'-Me-acridine-9-carboxylate (94 mg, 0.21 mmol), 1,3-propane sultone (2.6 g, 100 equivalents) and sodium bicarbonate (0.17 g, 10 equivalents) was heated in an oil bath at 140-145° C. under a nitrogen atmosphere. After 2 hours, the reaction was cooled to room temperature and diluted with 30 mL of a 1:1 mixture of ethyl acetate and hexanes. The mixture was sonicated to disperse the gum to a yellow powder and after the powder settled, the solvent was decanted. The yellow powder was rinsed several times with ethyl acetate/hexanes and then dried under vacuum to afford NSP-2'-($CH_2OCH_2CH_2OMe$)-6'-Me-AE methyl ester. MALDT-TOF MS 581.9 obs.

The crude acridinium ester was suspended in 4 mL of 1 N HCl and refluxed under nitrogen. After 2.5 h, HPLC analysis using a C18 column (4.6×30 mm) and a 30 minute gradient of 10→70% MeCN/water (each containing 0.05% TFA), at a flow rate of 1.0 mL/min and UV-detection at 260 nm, showed product, from complete hydrolysis of the methyl ester, eluting at Rt=13.4 minutes. (MALDI-TOF MS 567.2 obs.). The crude product was purified by preparative HPLC using a 30×300 mm, C18 column and the above gradient at a solvent flow rate of 20 ml/min. The product fraction was collected, frozen at −80° C. and lyophilized to dryness. Yield=77 mg (64%), yellow powder.

g) Synthesis of NSP-2'-($CH_2OCH_2CH_2OMe$)-6'-Me-AE-NHS

A solution of NSP-2'-($CH_2OCH_2CH_2OMe$)-6'-Me-AE (7.1 mg, 12.5 umoles) in DMF (dimethylformamide, 1 mL) was treated with diisopropylethylamine (6.4 uL, 3 equivalents) and TSTU (O—N-succinimidyluranium tetrafluoroborate, 5.6 mg, 1.5 equivalents). The reaction was stirred at room temperature. After 15 minutes HPLC analysis as described in (f) showed complete conversion to product eluting at 14.7 minutes (MALDI-TOF MS 665.2 obs.). The product was purified by preparative HPLC as described in (f). The product fraction was collected, frozen at −80° C. and lyophilized to dryness.

h) Synthesis of NSP-2'-($CH_2OCH_2CH_2OMe$)-6'-Me-AE-HEG

A solution of NSP-2'-($CH_2OCH_2CH_2OMe$)-6'-Me-AE (44 mg, 77.5 umoles) in DMF (dimethyl formamide, 2 mL) was treated with diisopropylethylamine (20 uL, 1.5 equivalents) and TSTU (26 mg, 1.1 equivalents). The reaction was stirred at room temperature. After 30 minutes, HPLC analysis as described in (f) showed complete conversion to the NHS ester. This DMF solution was then added drop wise to a solution of diamino-HEG (U.S. Pat. No. 6,664,043 B2, 0.1 g, 5 equivalents) in DMF (2 mL). The reaction was stirred at room temperature. After an additional 30 minutes, HPLC analysis as described in (f) showed complete conversion to product eluting at Rt=12.5 minutes (MALDI-TOF MS 830.5 obs.). The product was purified by preparative HPLC as described in (f). The product fraction was collected, frozen at −80° C. and lyophilized to dryness. Yield=51 mg (70%), yellow viscous oil.

i) Synthesis of NSP-2'-($CH_2OCH_2CH_2OMe$)-6'-Me-AE-HEG-glutarate and its NHS ester A solution of NSP-2'-($CH_2OCH_2CH_2OMe$)-6'-Me-AE-HEG (30 mg, 0.032 mmol) in methanol (3 mL) was treated with diisopropylethylamine (28 uL, 5 equivalents) and glutaric anhydride (18 mg, 5 equivalents). The reaction was stirred at room temperature. After 30 minutes, HPLC analysis as described in (f) showed ~80% conversion to product eluting at Rt=13.9 minutes An additional 2.5 equivalents each of diisopropylethylamine (14 uL) and glutaric anhydride (9 mg) was added and the reaction was continued for an additional 30 minutes. The reaction was then diluted with toluene (5 mL) and evaporated to dryness. The residue was dissolved in DMF (2 mL) and treated with diisopropylethylamine (28 uL, 5 equivalents) and TSTU (48 mg, 5 equivalents). The reaction was stirred at room temperature and after one hour, HPLC analysis as described in (f) showed complete conversion to product eluting at Rt=15 minutes (MALDI-TOF MS 1042.0 obs.). The product was purified by preparative HPLC as described in (f). The product fraction was collected, frozen at −80° C. and lyophilized to dryness. Yield=21.6 mg (65%), yellow oily solid.

j) Synthesis of NSP-2'-(CH$_2$OCH$_2$CH$_2$OMe)-6'-Me-AE-HEG-Cortisol

A solution of cortisol-3-CMO (Sigma, 4.6 mg, 10.6 umoles) in DMF (0.5 mL) was treated with diisopropylethylamine (2.2 uL, 1.2 equivalents) and HATU (4.8 mg, 1.2 equivalents). After stirring for 5 minutes, a solution of NSP-2'-(CH$_2$OCH$_2$CH$_2$OMe)-6'-Me-AE-HEG (5 mg, 5.3 umoles) was added in DMF (1 mL) along with diisopropylethylamine (2 uL, 2 equivalents). The reaction was stirred at room temperature. After 2 hours, HPLC analysis as described in (f) showed product eluting at Rt=17.8 minutes (MALDI-TOF MS 1249.2 obs.). The product was purified by preparative HPLC as described in (f). The product fraction was collected, frozen at −80° C. and lyophilized to dryness. Yield=4.8 mg (73%), yellow powder.

The following reactions describe the synthesis of NSP-2'-(CH$_2$OCH$_2$CH$_2$OMe)-6'-Me-AE-NHS, NSP-2'-(CH$_2$OCH$_2$CH$_2$OMe)-6'-Me-AE HEG, NSP-2'-(CH$_2$OCH$_2$CH$_2$OMe)-6'-Me-AE HEG-glutarate NHS ester and NSP-2'-(CH$_2$OCH$_2$CH$_2$OMe)-6'-Me-AE HEG-cortisol.

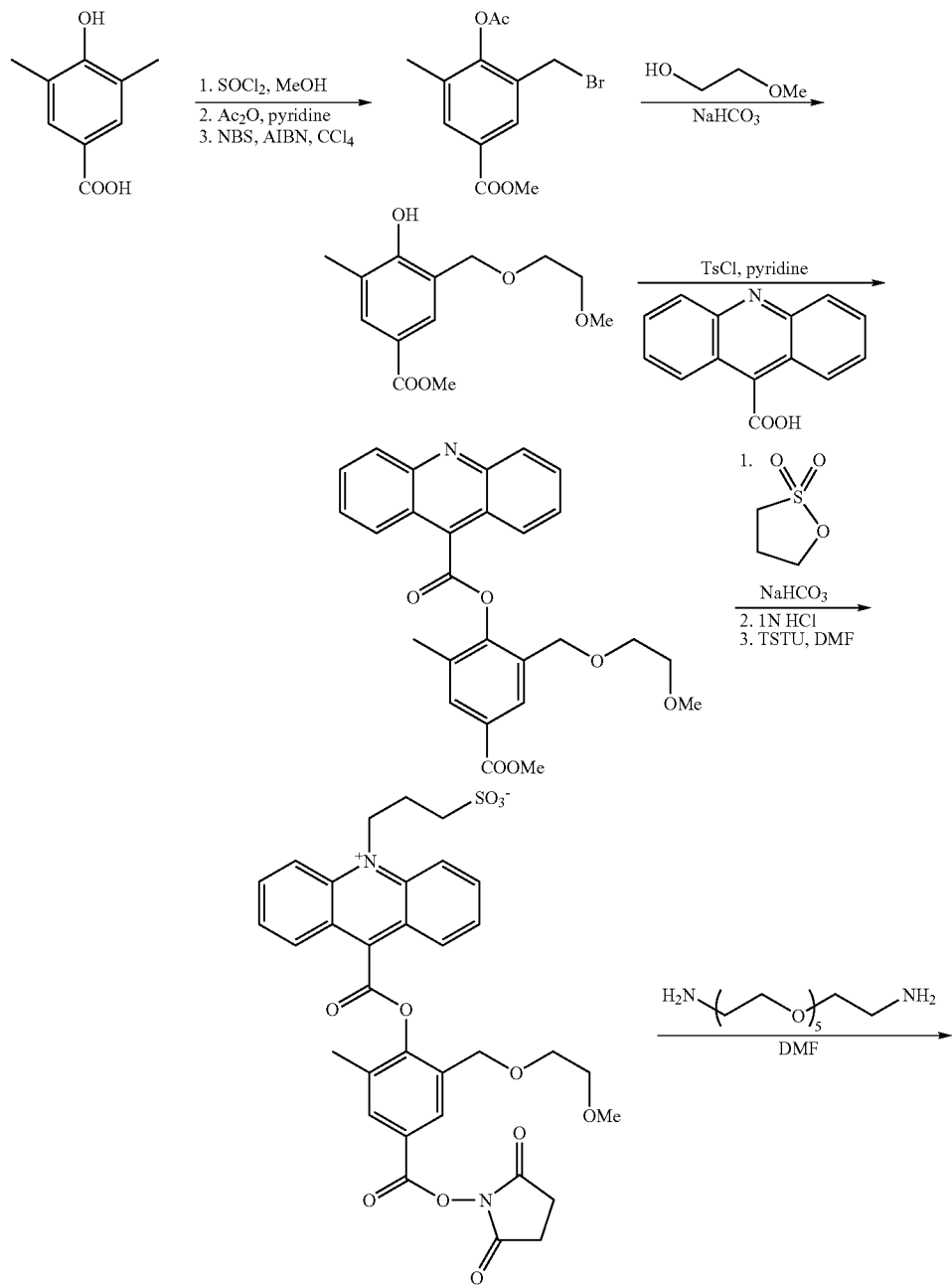

-continued

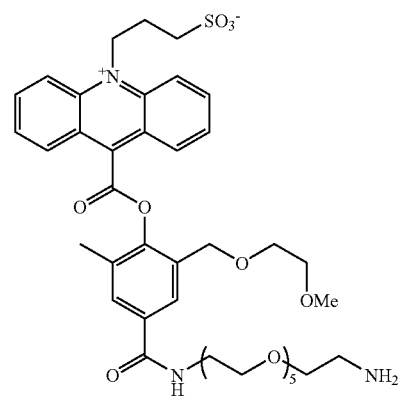
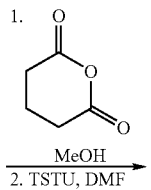
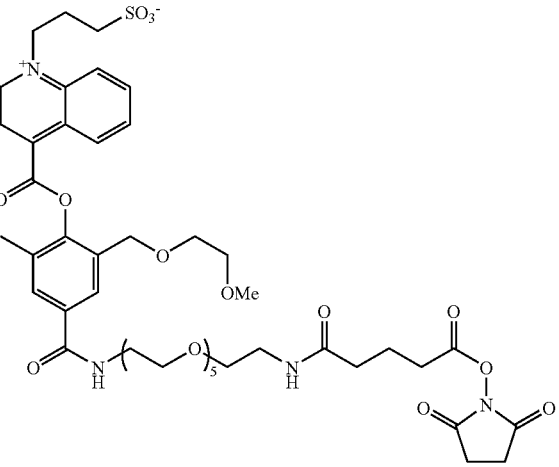

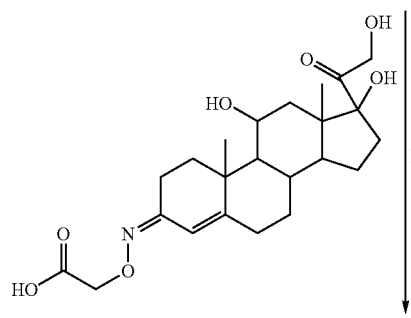

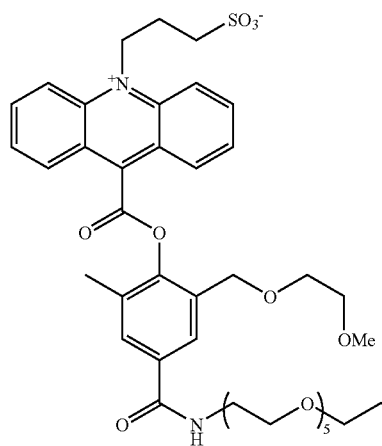

Example 2

Synthesis of NSP-2'-(CH$_2$OMe)-6'-Me-AE, NSP-2'-(CH$_2$OMe)-6'-Me-AE-HEG, NSP-2'-(CH$_2$OMe)-6'-Me-AE HEG-glutarate NHS ester and NSP-2'-(CH$_2$OMe)-6'-Me-AE HEG-cortisol a) Synthesis of methyl 3-methoxymethyl-4-hydroxy-5-methylbenzoate

A suspension of crude methyl 4-acetoxy-3-bromomethyl-5-methylbenzoate (4.63 g, 0.00154 mol) in methanol (100 mL) was mixed with sodium bicarbonate (6.48 g, 5 equivalents). The mixture was refluxed under a nitrogen atmosphere. After 1.5 hours, TLC analysis showed complete conversion. The reaction was cooled to room temperature and evaporated to dryness. The residue was partitioned between ethyl acetate (100 mL) and water (100 mL). The ethyl acetate layer was separated and washed with water. It was then dried over anhydrous magnesium sulfate, filtered and evaporated to dryness. The crude product (1.5 g) was purified by flash chromatography on silica using 10% ethyl acetate/hexanes as eluent. Purified Yield=0.833 g (40%), white waxy solid.

b) Synthesis of 2'-(CH$_2$OMe)-4'-methoxycarbonylphenyl-6'-Me-acridine 9-carboxylate A suspension of acridine-9-carboxylic acid (0.423 g, 1.9 mmol) in anhydrous pyridine (15 mL) was treated with p-toluenesulfonyl chloride (362 mg, 1.9 mmol). The reaction was stirred vigorously under a nitrogen atmosphere. After 10-15 minutes a solution of methyl 3-methoxymethyl-4-hydroxy-5-methylbenzoate (0.2 g, 0.95 mmol) in pyridine (5 mL) was added and the resulting reaction was stirred at room temperature for 5 days. The solvent was then removed under reduced pressure and the residue was dissolved in chloroform (50 mL). The chloroform solution was washed repeatedly with saturated aqueous sodium bicarbonate until the aqueous layer was clear. The chloroform solution was then washed with 1 N HCl and water. It was then dried over anhydrous magnesium sulfate and filtered. The filtrate was concentrated under reduced pressure to afford 0.41 g of crude product which was purified by preparative TLC on silica using 10% ethyl acetate/chloroform. Purified Yield=300 mg (76%), yellow powder, MALDI-TOF MS 414.9 obs.

c) Synthesis of NSP-2'-(CH$_2$OMe)-6'-Me-AE

A mixture of 2'-(CH$_2$OMe)-4'-methoxycarbonylphenyl-6'-Me-acridine-9-carboxylate (0.1 g, 0.24 mmol), 1,3-propane sultone (2.94 g, 100 equivalents) and sodium bicarbonate (0.2 g, 10 equivalents) was heated in an oil bath at 140-150° C. After 45 minutes the reaction solidified. A small portion was withdrawn, dissolved in methanol and analyzed by HPLC using a C18 column (4.6×30 mm) and a 30 minute gradient of 10→70% MeCN/water (each containing 0.05% TFA), at a flow rate of 1.0 mL/min and UV-detection at 260 nm as described in Example 1 (f). Product was observed eluting at Rt=15.5 minutes. The reaction was cooled to room temperature and 25-30 mL of 1:1 ethyl acetate/hexanes was added. The mixture was sonicated to disperse the gum to a yellow powder and after the powder settled, the solvent was decanted. The yellow powder was rinsed several times with ethyl acetate/hexanes and then dried under vacuum. The crude acridinium ester was suspended in 20 mL of 1 N HCl and refluxed under nitrogen. After 1.5 h, HPLC analysis, showed product from complete hydrolysis of the methyl ester, eluting at Rt=13.0 minutes. (MALDI-TOF MS 524.1 obs.). The crude product was purified by preparative HPLC using a 30×300 mm C18 column and the above gradient at a flow rate of 20 ml/min. The product fraction was collected, frozen at −80° C. and lyophilized to dryness. Yield=63.6 mg (60%), yellow powder.

d) Synthesis of NSP-2'-(CH$_2$OMe)-6'-Me-AE-HEG

A solution of NSP-2'-(CH$_2$OMe)-6'-Me-AE (64 mg, 121.4 umoles) in DMF (6 mL) was treated with diisopropylethylamine (32 uL, 1.5 equivalents) and TSTU (40 mg, 1.1 equivalents). The reaction was stirred at room temperature. After 30 minutes, HPLC analysis as described in (c) showed complete conversion to the NHS ester eluting at Rt=14 minutes. This DMF solution was then added drop wise to a solution of diamino-HEG (0.17 g, 5 equivalents) in DMF (3 mL). The reaction was stirred at room temperature. After an additional 15 minutes, HPLC analysis as described in (c) showed complete conversion to product eluting at Rt=12.4 minutes (MALDI-TOF MS 786.1 obs.). The product was purified by preparative HPLC as described in (c). The product fraction was collected, frozen at −80° C. and lyophilized to dryness. Yield=61 mg (64%), yellow viscous oil.

e) Synthesis of NSP-2'-(CH$_2$OMe)-6'-Me-AE-HEG-glutarate and its NHS ester

A solution of NSP-2'-(CH$_2$OMe)-6'-Me-AE-HEG (30 mg, 33.4 umoles) in methanol (3 mL) was treated with diisopropylethylamine (11.6 uL, 66.7 umoles) and glutaric anhydride (7.6 mg, 66.7 umoles). The reaction was stirred at room temperature. After 30 minutes, additional diisopropylethylamine (11.6 uL) and glutaric anhydride (7.6 mg) was added and the reaction was continued for an additional 60 minutes. HPLC analysis as described in (c) showed clean conversion to product eluting at Rt=13.6 minutes (MALDI-TOF MS 899.0 obs.). The reaction was then diluted with toluene (5 mL) and evaporated to dryness. The residue was dissolved in DMF (2 mL) and treated with diisopropylethylamine (29 uL, 5 equivalents) and TSTU (57 mg, 5 equivalents). The reaction was stirred at room temperature and after 30 minutes, HPLC analysis as described in (c) showed complete conversion to product eluting at Rt=14.9 minutes (MALDI-TOF MS 998.6 obs.). The product was purified by preparative HPLC as described in (c). The product fraction was collected, frozen at −80° C. and lyophilized to dryness. Yield=33.4 mg (100%), yellow oily solid.

f) Synthesis of NSP-2'-(CH$_2$OMe)-6'-Me-AE-HEG-Cortisol

A solution of cortisol-3-CMO (Sigma, 4.8 mg, 11.02 umoles) in DMF (0.5 mL) was treated with diisopropylethylamine (2.1 uL, 1.1 equivalents) and HATU (5.0 mg, 1.2 equivalents). After stirring for 5 minutes, a solution of NSP-2'-(CH$_2$OMe)-6'-Me-AE-HEG (5 mg, 5.6 umoles) was added in DMF (1 mL) along with diisopropylethylamine (2 uL, 2 equivalents). The reaction was stirred at room temperature. After 0.5 hours, HPLC analysis as described in (c) showed product eluting at Rt=17.8 minutes (MALDI-TOF MS 1204.5 obs.). The product was purified by preparative HPLC as described in (c). The product fraction was collected, frozen at −80° C. and lyophilized to dryness. Yield=5.1 mg (76%), yellow powder.

The following reactions describe the synthesis of NSP-2'-(CH$_2$OMe)-6'-Me-AE, NSP-2'-(CH$_2$OMe)-6'-Me-AE HEG, NSP-2'-(CH$_2$OMe)-6'-Me-AE HEG-glutarate NHS ester and NSP-2'-(CH$_2$OMe)-6'-Me-AE HEG-cortisol.

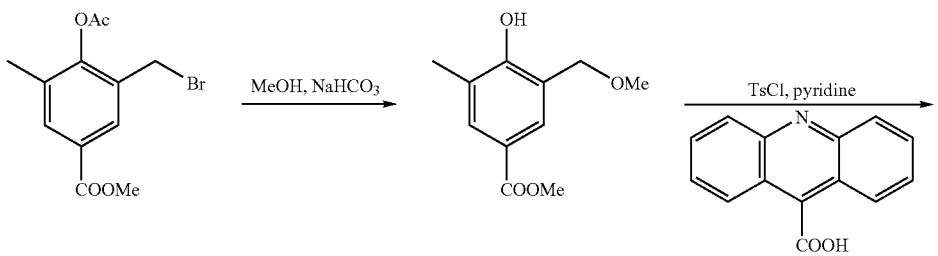

-continued
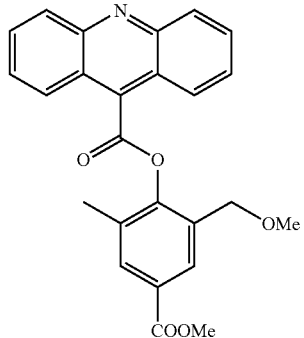
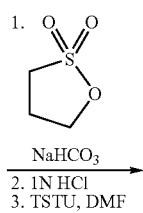
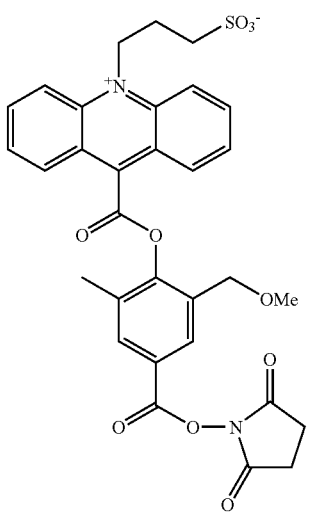
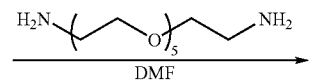
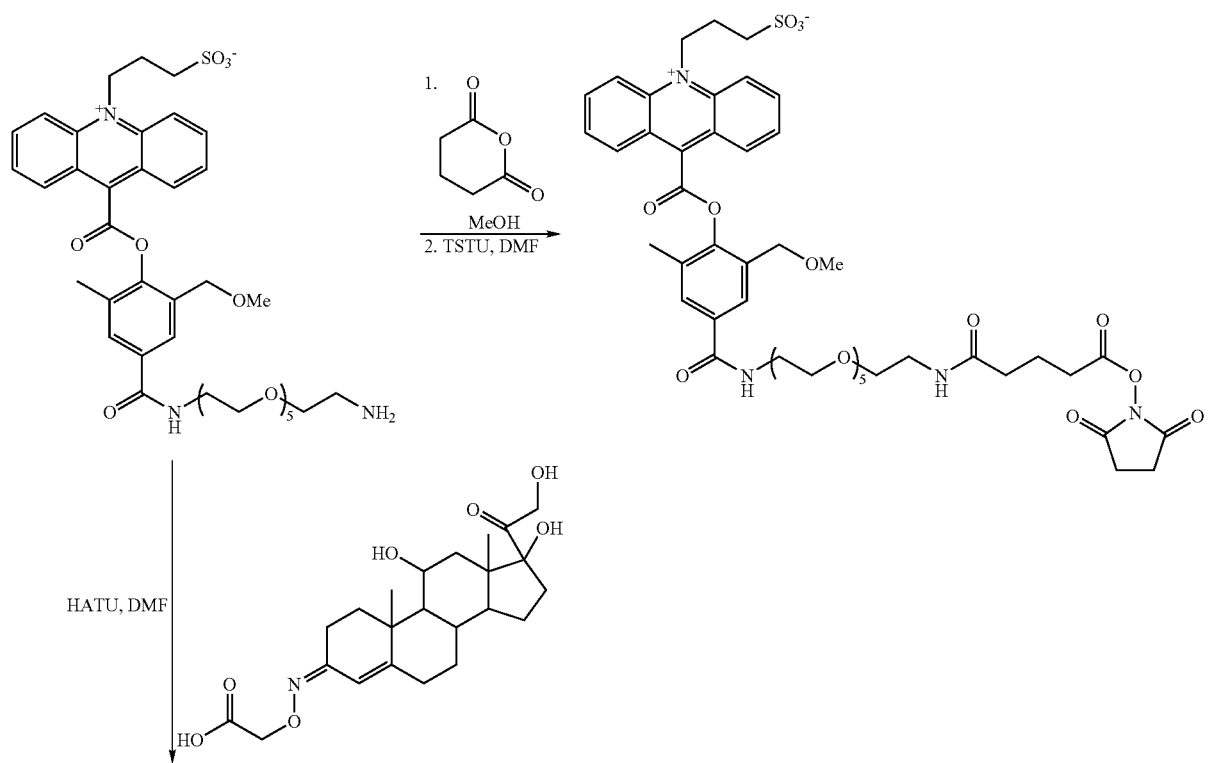

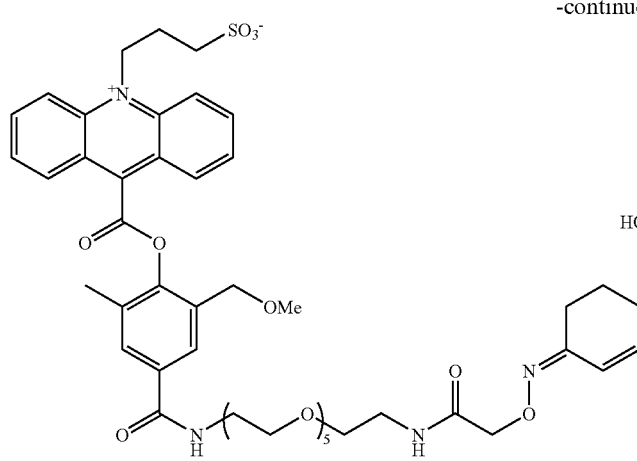

Example 3

Synthesis of NSP-2'-(CH$_2$O[CH$_2$CH$_2$O]$_2$CH$_2$CH$_2$OMe)-6'-Me-AE a) Synthesis of methyl 3-(CH$_2$O[CH$_2$CH$_2$O]$_2$CH$_2$CH$_2$OMe)-4-hydroxy-5-methylbenzoate Methoxytri(ethylene) glycol (Aldrich, 0.295 g, 1.8 mmol) in anhydrous tetrahydrofuran (THF, 10 mL) was cooled in an ice-bath under a nitrogen atmosphere and treated with sodium hydride (72 mg, 1.8 mmol, 60% dispersion). The reaction was stirred at 0° C. for 20 minutes and then an ice-cold solution of methyl 4-acetoxy-3-bromomethyl-5-methylbenzoate (0.9 mmol, 270 mg) was added in THF (3 mL). The reaction was stirred at 0° C. for 30 minutes by which time, TLC analysis on silica showed complete consumption of starting material. The reaction was then quenched with methanol (5 mL) and ethyl acetate (5 mL). The reaction mixture was then evaporated to dryness by rotary evaporation. The residue was dissolved in chloroform (50 mL) and washed with aqueous sodium bicarbonate and brine. it was then dried over anhydrous magnesium sulfate, filtered and evaporated to dryness. The crude product (0.44 g) was purified by preparative TLC using 2% methanol/chloroform. Yield=0.118 g (40%), oil, MALDI-TOF MS 366 obs. M+Na$^+$).

b) Synthesis of acridine-2'-(CH$_2$O[CH$_2$CH$_2$O]$_2$CH$_2$CH$_2$OMe)-4'-methoxycarbonylphenyl-6'-Me-acridine-9-carboxylate A solution of methyl 3-(CH$_2$O[CH$_2$CH$_2$O]$_2$CH$_2$CH$_2$OMe)-4-hydroxy-5-methylbenzoate (20 mg, 58.5 umoles) in pyridine (1 mL) at 0° C. was treated with acridine-9-carbonyl chloride (27 mg, 2 equivalents). The reaction was warmed to room temperature as the ice-bath melted and stirred under a nitrogen atmosphere for 3 days. The solvent was then removed under reduced pressure and the residue was dissolved in chloroform (30 mL). This solution was washed with saturated aqueous sodium bicarbonate, saturated aqueous ammonium chloride and brine. It was then dried over anhydrous magnesium sulfate, filtered and evaporated to dryness. The product was purified by preparative TLC on silica gel using 20% ethyl acetate/chloroform. Yield=11.6 mg (36%), MALDI-TOF MS 548.9 obs.

c) Synthesis of NSP-2'-(CH$_2$O[CH$_2$CH$_2$O]CH$_2$CH$_2$OMe)-6'-Me-AE

A mixture of 2'-(CH$_2$O[CH$_2$CH$_2$O]CH$_2$CH$_2$OMe)-4'-methoxycarbonylphenyl-6'-Me-acridine-9-carboxylate (11.6 mg, 21.2 umoles), 1,3-propane sultone (0.5 g, 200 equivalents) and sodium bicarbonate (36 mg, 20 equivalents) was heated in an oil bath at 140-150° C. After 3 hours the reaction was cooled to room temperature and, a small portion was withdrawn, dissolved in methanol and analyzed by HPLC using a C18 column (4.6×30 mm) and a 30 minute gradient of 10→70% MeCN/water (each containing 0.05% TFA), at a flow rate of 1.0 mL/min and UV-detection at 260 nm. Product was observed eluting at Rt=16.3 minutes. The reaction mixture was diluted with 10 mL of 1:1 ethyl acetate/hexanes. The mixture was sonicated to disperse the gum to a yellow powder and after the powder settled, the solvent was decanted. The yellow powder was rinsed twice with ethyl acetate/hexanes and then dried under vacuum. The crude acridinium ester was suspended in 3.5 mL of 1 N HCl and refluxed under nitrogen. After 1.5 h, HPLC analysis, showed product from complete hydrolysis of the methyl ester, eluting at Rt=13.6 minutes. (MALDI-TOF MS 657.9 obs.). The crude product was purified by preparative HPLC using a 30×300 mm C18 column and the above gradient at a flow rate of 20 ml/min. The product fraction was collected, frozen at −80° C. and lyophilized to dryness. Yield=4.5 (32%), yellow powder.

The following reactions describe the synthesis of NSP-2'-(CH$_2$O[CH$_2$CH$_2$O]$_2$CH$_2$CH$_2$OMe)-6'-Me-AE.

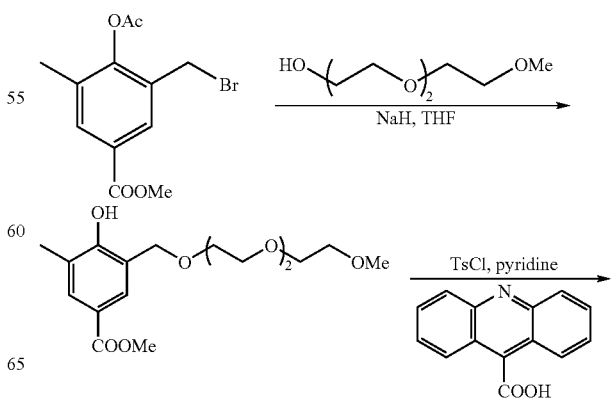

-continued

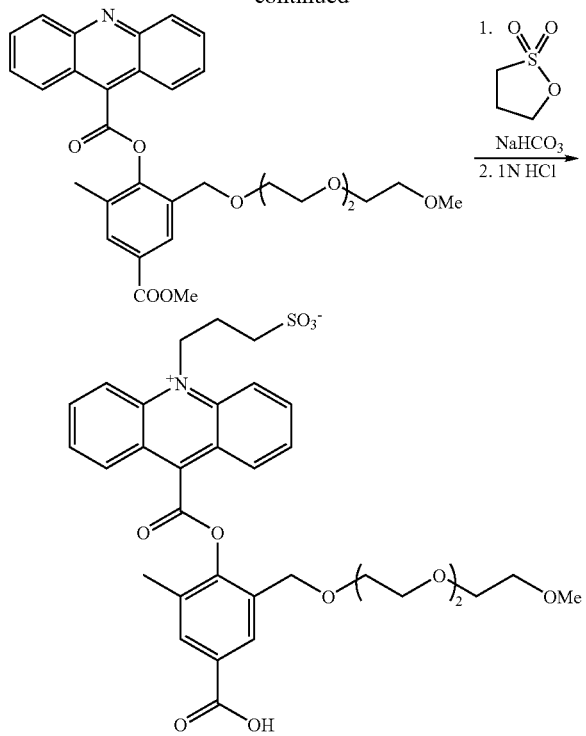

Example 4

Synthesis of NSP-2,7-(OMHEG)₂-2'-(CH₂O[CH₂CH₂O]₂CH₂CH₂OMe)-6'-Me-AE, NSP-2,7-(OMHEG)₂-2'-(CH₂OMe)-6'-Me-AE and its NHS ester a) Synthesis of 2,7-dimethoxy acridine methyl ester

Crude 2,7-dimethoxyacridine-9-carboxylic acid (U.S. Pat. No. 5,521,103, 0.5 g) was suspended in thionyl chloride (5 mL) and the suspension was refluxed under a nitrogen atmosphere. After one hour, it was cooled to room temperature and hexanes (40 mL) was added. The precipitated solid was collected by filtration and rinsed with hexanes. The product (~0.5 g) was then dried under vacuum. It was then dissolved in an ice cold solution of 4:1, pyridine/methanol and the reaction stirred at 0° C. for one hour and was then warmed to room temperature for 36 h. The solvent was then removed under reduced pressure and the residue was dissolved in chloroform (50 mL). This solution was washed with 1N HCl followed by saturated aqueous sodium bicarbonate and brine. The chloroform layer was then dried over anhydrous magnesium sulfate, filtered and evaporated to dryness. Yield=231 mg, reddish-yellow powder.

b) Synthesis of 2,7-hydroxy acridine methyl ester

A solution of 2,7-dimethoxy acridine methyl ester (0.23 g) in dichloromethane (20 mL) was treated with a dichloromethane solution of boron tribromide (1M, 15 mL). The reaction was stirred at room temperature for 48 h. It was then cooled in an ice-bath and methanol (20 mL) was added slowly. After the addition, the reaction was warmed to room temperature and stirred for 24 hours. The reaction was then neutralized with the addition of solid sodium bicarbonate and the suspension was evaporated to dryness. The residue was partitioned between ethyl acetate (50 mL) and water (50 mL). The ethyl acetate layer was separated, washed with brine and dried over anhydrous magnesium sulfate. It was then filtered and evaporated to dryness. Yield=80 mg, MALDI-TOF MS 270.0 obs.

c) Synthesis of 2,7-(OMHEG)₂-acridine methyl ester

A solution of 2,7-dihydroxyacridine methyl ester (80 mg, 0.296 mmol) in anhydrous THF (10 mL) was treated with methoxyhexa(ethylene) glycol monotosylate (US 2005/0221390A1, 0.4 g, 3 equivalents) and cesium carbonate (96.5 mg, 3 equivalents). The reaction was refluxed under a nitrogen atmosphere. After 4 hours, HPLC analysis using a C18 column (4.6×30 mm) and a 30 minute gradient of 10→70% MeCN/water (each containing 0.05% TFA), at a flow rate of 1.0 mL/min and UV-detection at 260 nm, showed complete conversion to product eluting at 18.2 minutes (MALDI-TOF MS 827.0 obs.). The reaction was cooled to room temperature and evaporated to dryness. The residue was partitioned between chloroform (30 mL) and saturated aqueous ammonium chloride solution. The chloroform layer was separated and washed once more with ammonium chloride solution followed by brine. It was then dried over anhydrous magnesium sulfate, filtered and evaporated to dryness. The crude product (0.32 g) was purified by preparative TLC on silica using 5% methanol/chloroform. Yield=40 mg (16%), oily solid.

d) Synthesis of 2,7-(OMHEG)₂-acridine-9-carboxylic acid

A solution of 2,7-(OMHEG)₂-acridine methyl ester stirred in 2 N potassium hydroxide at room temperature for 16 hours by which time TLC analysis showed complete hydrolysis. The reaction was then cooled in an ice-bath and neutralized with concentrated HCl. This solution was evaporated to dryness and the residue was dissolved in methanol (5 mL), filtered and evaporated to dryness. Yield=57 mg (100%).

e) Synthesis of 2,7-(OMHEG)₂-2'-(CH₂O[CH₂CH₂O]CH₂CH₂OMe)-4'-methoxycarbonylphenyl-6'-Me-acridine-9-carboxylate A solution of 2,7-(OMHEG)₂-acridine-9-carboxylic acid (54 mg, 66.4 umoles) in pyridine (1 mL) was treated with p-toluenesulfonyl chloride (32 mg, 2.5 equivalents). The reaction was stirred at room temperature under a nitrogen atmosphere for 10 minutes and then methyl 3-(CH₂O[CH₂CH₂O]₂CH₂CH₂OMe)-4-hydroxy-5-methylbenzoate (20 mg, 58.5 umoles) in pyridine (1 mL) was added. The reaction was stirred at room temperature for 3 days. The solvent was then removed under reduced pressure and the residue was dissolved in MeCN (5 mL). HPLC analysis using a C18 column (4.6×30 mm) and a 30 minute gradient of 10→70% MeCN/water (each containing 0.05% TFA), at a flow rate of 1.0 mL/min and UV-detection at 260 nm, showed ~50% conversion to product eluting at Rt=22.6 minutes (MALDI-TOF MS 1140.6 obs.). The product was purified by preparative TLC on silica using 5% methanol/chloroform. Yield=10 mg, 36% based on 50% conversion).

f) Synthesis of NSP-2,7-(OMHEG)₂-2'-(CH₂O[CH₂CH₂O]CH₂CH₂OMe)-6'-Me-AE

A mixture of 2,7-(OMHEG)₂-2'-(CH₂O[CH₂CH₂O]CH₂CH₂OMe)-4'-methoxycarbonylphenyl-6'-Me-acridine- 9-carboxylate (10 mg, 8.8 umoles), 1,3-propane sultone (0.2 g, 200 equivalents) and sodium bicarbonate (15 mg, 20 equivalents) was heated in an oil bath at 140-150° C. After one hour the reaction was cooled to room temperature and diluted with 20 mL of 1:1 ethyl acetate/hexanes. The mixture was sonicated to disperse the gum to a yellow powder and after the powder settled, the solvent was decanted. The yellow powder was rinsed twice with ethyl acetate/hexanes and then dried under vacuum. The crude acridinium ester was suspended in 3.0 mL of 1 N HCl and refluxed under nitrogen. After 1.5 h, HPLC analysis as described in (e) showed product from complete hydrolysis of the methyl ester, eluting at Rt=16.7 minutes. (MALDI-TOF MS 1249.7 obs.). The crude product was purified by preparative HPLC using a 30×300 mm C18 column and the above gradient at a flow rate of 20 ml/min. The product fraction was collected, frozen at −80° C. and lyophilized to dryness.

g) Synthesis of 2,7-(OMHEG)$_2$-2'-(CH$_2$OMe)-4'-methoxycarbonylphenyl-6'-Me-acridine-9-carboxylate A solution of 2,7-(OMHEG)$_2$-acridine-9-carboxylic acid (120 mg, 146 umoles) in pyridine (7 mL) was treated with p-toluenesulfonyl chloride (56 mg, 2.0 equivalents). The reaction was stirred at room temperature under a nitrogen atmosphere for 5 minutes and then methyl 3-methoxymethyl-4-hydroxy-5-methylbenzoate (61 mg, 2 equivalents) in pyridine (3 mL) was added. The reaction was stirred at room temperature for 5 days. The solvent was then removed under reduced pressure and the residue was dissolved in toluene (10 mL) and evaporated to dryness. The residue was dissolved in chloroform (5 mL). HPLC analysis using a C18 column (4.6× 30 mm) and a 30 minute gradient of 10→70% MeCN/water (each containing 0.05% TFA), at a flow rate of 1.0 mL/min and UV-detection at 260 nm, showed product eluting at Rt=22.8 minutes (MALDI-TOF MS 1005.8 obs.). The product was purified by preparative TLC on silica using 2% methanol/chloroform. Yield=70 mg, 62%, reddish-yellow oily solid.

h) Synthesis of NSP-2,7-(OMHEG)$_2$-2'-(CH$_2$OMe)-6'-Me-AE and its NHS ester

A mixture of 2,7-(OMHEG)$_2$-2'-(CH$_2$OMe)-4'-methoxycarbonylphenyl-6'-Me-acridine-9-carboxylate (70 mg), 1,3-propane sultone (1 g) and sodium bicarbonate (75 mg) was heated in an oil bath at 140-150° C. After 2 hours the reaction was treated with an additional 0.5 g of 1,3-propane sultone and 44 mg sodium bicarbonate and heated for one more hour. It was then cooled to room temperature and diluted with 20 mL of 1:1 ethyl acetate/hexanes. The mixture was sonicated to disperse the gum to a yellow powder and after the powder settled, the solvent was decanted. The yellow powder was rinsed twice with ethyl acetate/hexanes and then dried under vacuum. The crude acridinium ester was suspended in 20 mL of 1 N HCl and refluxed under nitrogen. After 1.5 h, HPLC analysis as described in (e) showed product from complete hydrolysis of the methyl ester, eluting at Rt=16.5 minutes. (MALDI-TOF MS 1114.3 obs.). The crude product was purified by preparative HPLC using a 30×300 mm C18 column and the above gradient at a flow rate of 20 ml/min. The product fraction was collected, frozen at −80° C. and lyophilized to dryness. Yield=29.5 mg (39%). The following reactions describe the synthesis of NSP-2,7-(OMHEG)$_2$-2'-(CH$_2$O[CH$_2$CH$_2$O]$_2$CH$_2$CH$_2$OMe)-6'-Me-AE, NSP-2,7-(OMHEG)$_2$-2'-(CH$_2$OMe)-6'-Me-AE and its NHS ester.

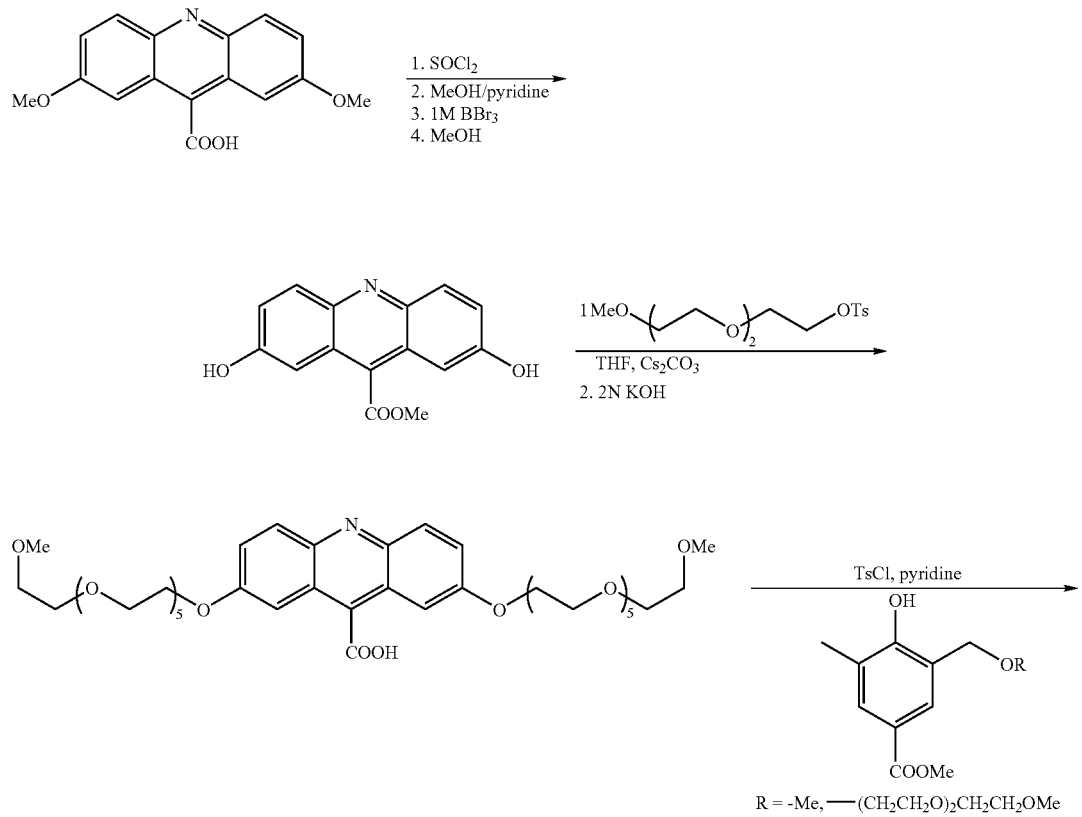

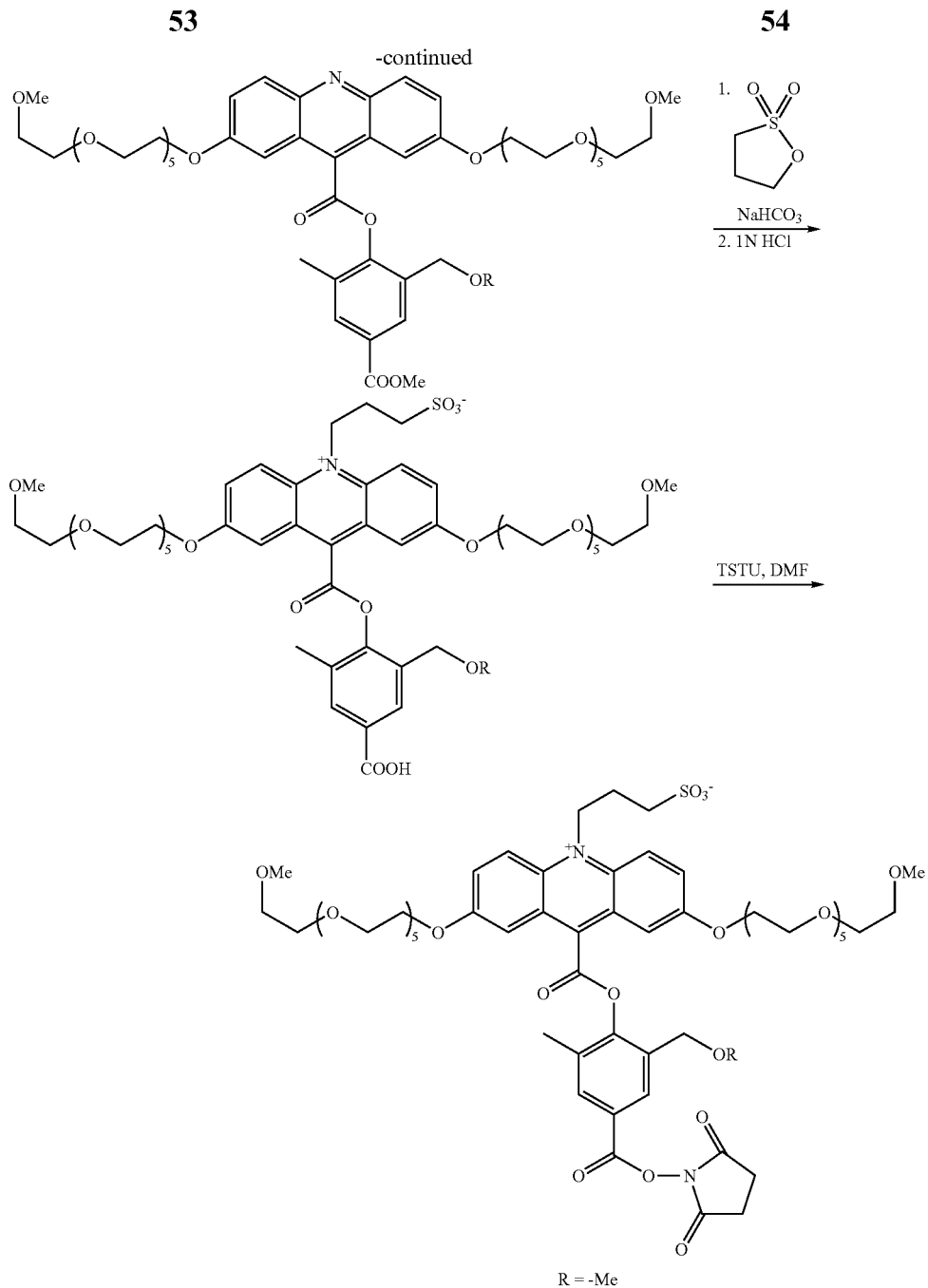

R = -Me

Example 5

Synthesis of NSP-2'-(CH$_2$OCH$_2$CH$_2$OMe)$_2$-6'-Me-AE a) Synthesis of methyl 4-acetoxy-3,5-bis(bromomethyl)benzoate

A solution of methyl 4-acetoxy-3,5-dimethylbenzoate (1.13 g, 0.0051 mol) in carbon tetrachloride (30 mL) was treated with AIBN (210 mg, 0.25 equivalent) and NBS (2.27 g, 2.5 equivalents). The reaction was refluxed under a nitrogen atmosphere for 6 hours. The reaction was then cooled to room temperature and diluted with chloroform (30 mL). This solution was washed with water (4×50 mL). The chloroform solution was then dried over anhydrous magnesium sulfate, filtered and evaporated to dryness to give the crude dibromide as a waxy solid. Yield=1.18 g. This material was used without purification in the next reaction.

b) Synthesis of methyl 3,5-(CH$_2$OCH$_2$CH$_2$OMe)$_2$-4-hydroxybenzoate

Crude methyl 4-acetoxy-3,5-bis(bromomethyl)benzoate (0.5 g) was mixed with ethyleneglycol monomethyl ether (20 mL) and sodium bicarbonate (0.55 g, 5 equivalents). The mixture was heated in an oil-bath at 90° C. for 3 hours, by which time TLC analysis indicated no starting material. The reaction was cooled to room temperature and evaporated to dryness by rotary evaporation. The residue was suspended in ethyl acetate (30-40 mL) and filtered. The filtrate was washed with saturated aqueous ammonium chloride solution. It was then dried over anhydrous magnesium sulfate, filtered and evaporated to dryness. The crude product (0.194 g) was purified by preparative TLC on silica gel using 40% ethyl acetate/ hexanes. Purified Yield=52 mg (viscous oil).

c) Synthesis of 2',6'-(CH$_2$OCH$_2$CH$_2$OMe)$_2$-4'-methoxycarbonylphenyl-acridine-9-carboxylate A suspension of acridine-9-carboxylic acid (71 mg, 0.317 mol) in pyridine (15 mL) was treated with p-toluenesulfonyl chloride (60 mg, 0.317 mmol). The reaction was stirred vigorously for 10 minutes and then solution of methyl 3,5-(CH$_2$OCH$_2$CH$_2$OMe)$_2$-4-hydroxybenzoate (52 mg, 0.159 mmol) was added in pyridine (5 mL). The resulting solution was stirred at room temperature under a nitrogen atmosphere for 4 days. The solvent was then removed under reduced pressure and the residue was dissolved in chloroform (40 mL) which was then washed with saturated aqueous sodium bicarbonate, saturated aqueous ammonium chloride and brine. It was then dried over anhydrous magnesium sulfate, filtered and evaporated to dryness. The crude product (74 mg) was purified by preparative TLC on silica using 1% MeOH/chloroform. Yield=51 mg (60%). MALDI-TOF MS 535.2 obs.

d) Synthesis of NSP-2',6'-(CH$_2$OCH$_2$CH$_2$OMe)$_2$-AE

A mixture of 2',6'-(CH$_2$OCH$_2$CH$_2$OMe)$_2$-4'-methoxycarbonylphenyl-6'-Me-acridine 9-carboxylate (50 mg, 94 umoles), 1,3-propane sultone (2.28 g, 200 equivalents) and sodium bicarbonate (158 mg, 20 equivalents) was heated in an oil bath at 140-150° C. After 2-3 hours the reaction was cooled to room temperature and, a small portion was withdrawn, dissolved in methanol and analyzed by HPLC using a C18 column (4.6×30 mm) and a 30 minute gradient of 10→70% MeCN/water (each containing 0.05% TFA), at a flow rate of 1.0 mL/min and UV-detection at 260 nm. Product was observed eluting at Rt=15.4 minutes. The reaction mixture was diluted with 30 mL of 1:1 ethyl acetate/hexanes. The mixture was sonicated to disperse the gum to a yellow powder and after the powder settled, the solvent was decanted. The yellow powder was rinsed twice with ethyl acetate/hexanes and then dried under vacuum. The crude acridinium ester was suspended in 20 mL of 1 N HCl and refluxed under nitrogen. After 2 h, HPLC analysis, showed product from complete hydrolysis of the methyl ester, eluting at Rt=13.0 minutes. (MALDI-TOF MS 643.5 obs.). The crude product was purified by preparative HPLC using a 30×300 mm C18 column and the above gradient at a flow rate of 20 ml/min. The product fraction was collected, frozen at −80° C. and lyophilized to dryness. Yield=30 mg (50%), yellow powder.

The following reactions describe the synthesis of NSP-2', 6'-(CH$_2$OCH$_2$CH$_2$OMe)$_2$-AE.

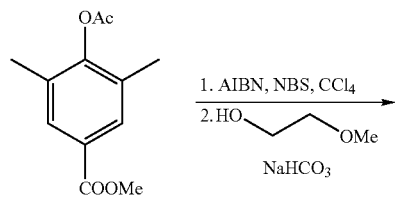

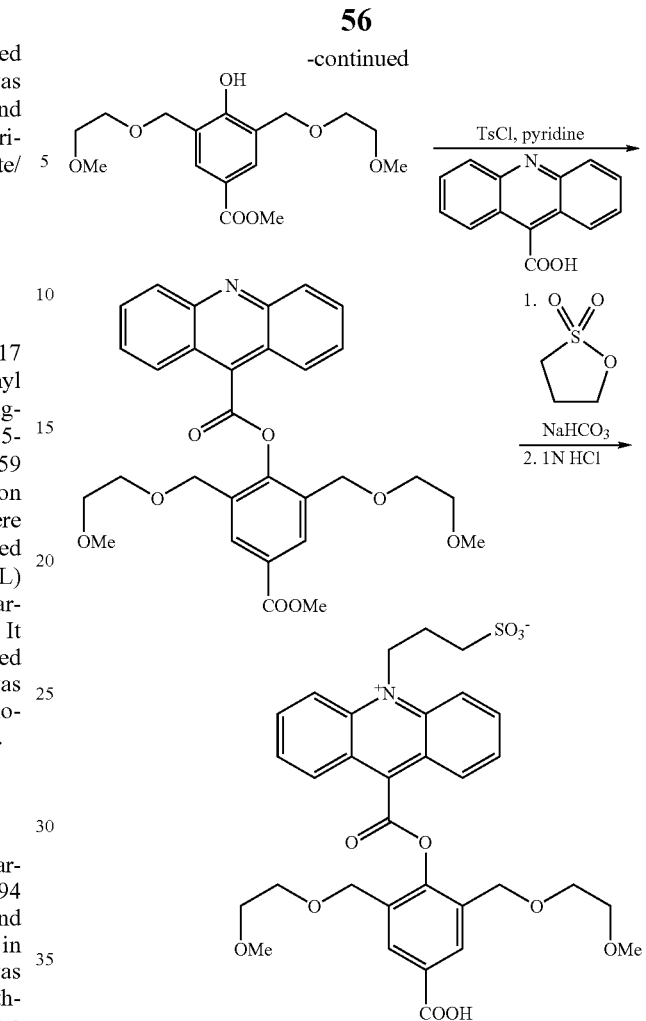

Example 6

Synthesis of NSP-2'-(CH$_2$OCHMe$_2$)-6'-Me-AE and its NHS ester a) Synthesis of methyl 3-isopropyloxymethyl-4-hydroxy-5-methylbenzoate A solution of crude methyl 4-acetoxy-3-bromomethyl-5-methylbenzoate (120 mg, 0.314 mmol) in dichloromethane (5 mL) was treated with 2-propanol (0.12 mL, 5 equivalents) followed by silver triflate (81 mg, 1 equivalent). The reaction was stirred at room temperature for 16 hours and was then filtered to remove silver salts. The filtrate was evaporated to dryness. The product methyl 3-isopropyloxymethyl-4-acetoxy-5-methylbenzoate was purified by preparative TLC on silica using 10% ethylacetate/hexanes to afford 75 mg of an oil solid which was dissolved in methanol and treated with sodium bicarbonate (113 mg, 5 equivalents). The reaction was refluxed under a nitrogen atmosphere for one hours and was then cooled to room temperature and evaporated to dryness. The residue was dissolved in ethyl acetate (10-15 mL) and was filtered. The filtrate was evaporated to dryness to afford 56 mg of crude product which was used as such without purification.

b) Synthesis of 2'-(CH$_2$OCHMe$_2$)-4'-methoxycarbonylphenyl-6'-Me-acridine-9-carboxylate A suspension of acridine-9-carboxylic acid (112 mg, 0.5 mmol) in pyridine (7 mL) was treated with p-toluenesulfonyl chloride (96.5 mg, 0.5 mmol). The suspension was stirred vigorously under a nitrogen atmosphere until clear and then a solution of methyl 3-isopropyloxymethyl-4-hydroxy-5-methylbenzoate (56 mg, 0.25 mmol) was added in pyridine (1 mL). The reaction was stirred at room temperature for 3 days. HPLC analysis of the crude reaction mixture using a C18 column (4.6×30 mm) and a 30 minute gradient of 10→70% MeCN/water (each containing 0.05% TFA), at a flow rate of 1.0 mL/min and UV-detection at 260 nm, showed product eluting at Rt=25.2 minutes (MALDI-TOF MS 443.9 obs.). The reaction mixture was evaporated to dryness and the residue was dissolved in chloroform (30 mL). This solution was washed with 1N HCl, saturated aqueous sodium bicarbonate and water. It was then dried over anhydrous magnesium sulfate, filtered and evaporated to dryness. The crude product (75 mg) was purified by preparative TLC on silica using 10% ethyl acetate/chloroform. Yield=32 mg (30%), oily solid.

c) Synthesis of NSP-2'-(CH$_2$OCHMe$_2$)-6'-Me-AE and its NHS ester

A mixture of 2'-(CH$_2$OCHMe$_2$)-4'-methoxycarbonylphenyl-6'-Me-acridine 9-carboxylate (32 mg, 72 umoles), 1,3-propane sultone (0.88 g, 100 equivalents) and sodium bicarbonate (61 mg, 10 equivalents) was heated in an oil bath at 140-150° C. After 2 hours the reaction was cooled to room temperature and, a small portion was withdrawn, dissolved in methanol and analyzed by HPLC using a C18 column (4.6×30 mm) and a 30 minute gradient of 10→70% MeCN/water (each containing 0.05% TFA), at a flow rate of 1.0 mL/min and UV-detection at 260 nm. Product was observed eluting at Rt=17.5 minutes (MALDI-TOF MS 565.8 obs). The reaction mixture was diluted with 20 mL of 1:1 ethyl acetate/hexanes. The mixture was sonicated to disperse the gum to a yellow powder and after the powder settled, the solvent was decanted. The yellow powder was rinsed twice with ethyl acetate/hexanes and then dried under vacuum. The crude acridinium ester was suspended in 10 mL of 10% HCl and refluxed under nitrogen. After 2 h, HPLC analysis, showed product from complete hydrolysis of the methyl ester, eluting at Rt=14.4 minutes. (MALDI-TOF MS 643.5 obs.). The crude product was purified by preparative HPLC using a 30×300 mm C18 column and the above gradient at a flow rate of 20 ml/min. The product fraction was collected, frozen at −80° C. and lyophilized to dryness. Yield=19.8 mg (50%), yellow powder.

The acridinium ester was dissolved in DMF (2 mL) and treated with diisopropylethylamine (9.4 uL, 1.5 equivalents) and TSTU (13 mg, 1.2 equivalents). The reaction was stirred at room temperature. After 30 minutes, HPLC analysis showed complete conversion to the NHS ester eluting at Rt=16.6 minutes (MALDI-TOF MS 649 obs.). The crude product was purified by preparative HPLC using a 30×300 mm C18 column and the above gradient at a flow rate of 20 ml/min. The product fraction was collected, frozen at −80° C. and lyophilized to dryness. Yield=12 mg (51%), yellow powder.

The following reaction describe the synthesis of NSP-2'-(CH$_2$OCHMe$_2$)-6'-Me-AE and its NHS ester.

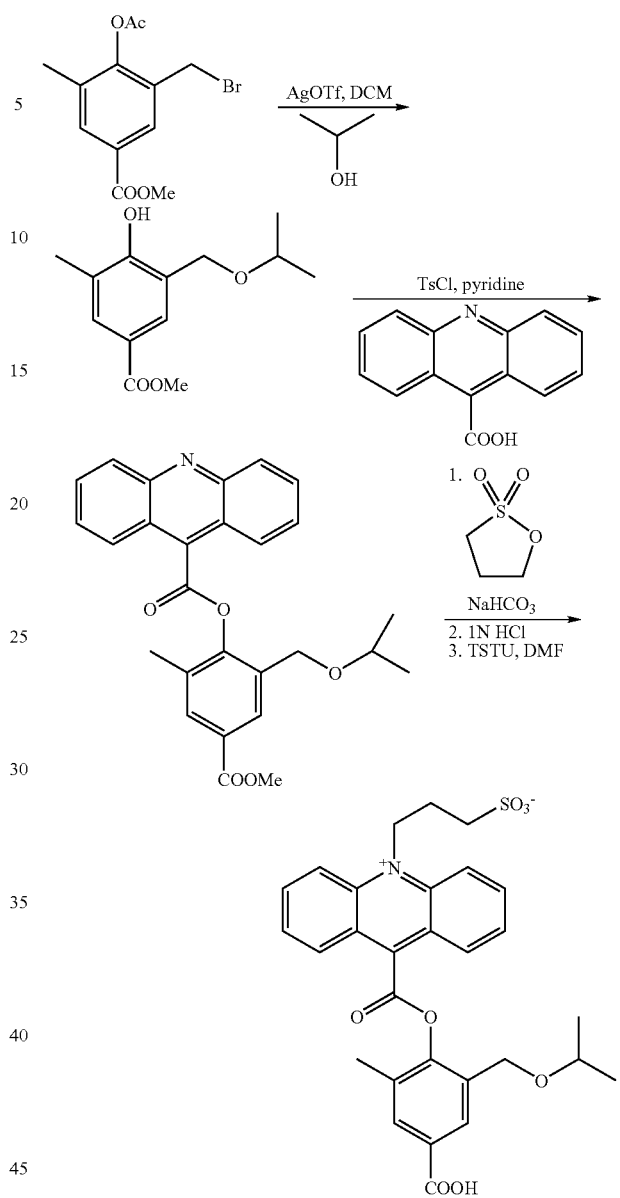

Example 7

Synthesis of NSP-2'-(CH$_2$CH[OMe]Me)-6'-Me-AE a) Synthesis of methyl 4-hydroxy-3-methylbenzoate A solution of 4-hydroxy-3-methylbenzoic acid (Matrix Scientific, 1 g) was dissolved in methanol and cooled in an ice-bath under a nitrogen atmosphere. Thionyl chloride (5 mL) was added slowly. The reaction was stirred at 0° C. for one hour and then warmed to room temperature and stirred for 16 hours. Solid sodium bicarbonate was then added to neutralize the acid and the mixture was evaporated to dryness. The residue was partitioned between ethyl acetate (75 mL and water (100 mL). The ethyl acetate layer was dried over anhydrous magnesium sulfate, filtered and evaporated to dryness to afford 1.0 g of product.

b) Synthesis of methyl 3-O-allyl-4-methylbenzoate

A solution of methyl 4-hydroxy-3-methylbenzoate (1 g, 0.006 mol) in acetone (50 mL) was treated with anhydrous potassium carbonate (1.656 g, 0.012 mol) and allyl bromide (0.78 mL, 0.009 mol). The reaction was refluxed under a nitrogen atmosphere. After 3 hours, TLC analysis indicated complete conversion. The reaction was cooled to room temperature and evaporated to dryness. The residue was partitioned between ethyl acetate (50 mL) and water (50 mL). The ethyl acetate layer was dried over anhydrous magnesium sulfate, filtered and evaporated to dryness. Yield=1.138 g (light brown oil).

c) Synthesis of methyl 4-hydroxy-3-allyl-5-methylbenzoate

A solution of methyl 3-O-allyl-4-methylbenzoate (1.138 g) in N,N-diethylaniline (5 mL) was heated in an oil bath at 200° C. under a nitrogen atmosphere. After 8 hours HPLC analysis HPLC using a C18 column (4.6×30 mm) and a 30 minute gradient of 10→70% MeCN/water (each containing 0.05% TFA), at a flow rate of 1.0 mL/min and UV-detection at 260 nm, showed ~80% conversion. The reaction was cooled to room temperature and diluted with ethyl acetate (75 mL). This solution was washed with 300 mL of 10% HCl followed by saturated aqueous sodium bicarbonate. The ethyl acetate layer was den dried over anhydrous magnesium sulfate, filtered and evaporated to dryness. The crude product (1.11 g) was purified by preparative TLC on silica using 30% ethyl acetate/hexanes. The product was obtained as a tan powder, yield=0.843 g (75%).

d) Synthesis of methyl 4-acetoxy-3-allyl-5-methylbenzoate

A solution of methyl 4-hydroxy-3-allyl-5-methylbenzoate (157 mg) in pyridine (5 mL) was cooled in an ice-bath under a nitrogen atmosphere and treated with acetic anhydride (1 mL). The reaction was stirred in the ice-bath for one hour and was then warmed to room temperature for 4 hours. The solvent was then removed under reduced pressure and the residue was suspended in anhydrous toluene (5-10 mL) and evaporated to dryness. The crude product was dissolved in ethyl acetate (30 mL) and washed with saturated aqueous ammonium chloride. It was then dried over anhydrous magnesium sulfate, filtered and evaporated to dryness to give a brown oil. Yield=0.176 g (quantitative).

e) Synthesis of methyl 4-hydroxy-3-(2-methoxypropyl)-5-methylbenzoate

A solution of methyl 4-acetoxy-3-allyl-5-methylbenzoate (175 mg, 0.75 mmol) in methanol (2 mL) was cooled in an ice-bath under a nitrogen atmosphere and treated with mercuric trifluoroacetate (322 mg, 1 equivalent). The reaction was stirred in the ice-bath for one hour by which time TLC analysis showed complete consumption of staring material. The reaction was then treated with 1 mL of 3 N NaOH and after vigorous stirring for 2 minutes, a solution of sodium borohydride (0.5 M, 1 mL) in 3 N NaOH was added. The back suspension was stirred for 5 minutes in the ice-bath and then ethyl acetate (25 mL) was added. After stirring for an additional 5 minutes, the ethyl acetate solution was decanted and then washed twice with saturated aqueous ammonium chloride. It was then dried over anhydrous magnesium sulfate, filtered and evaporated to dryness. The crude product (141 mg, oil) was purified by preparative TLC on silica using 15% ethyl acetate/hexanes. Purified Yield=82 mg (~50%), MALDI-TOF 239 obs.

f) Synthesis of 2'-(CH₂CH[OMe]Me)-4'-methoxycarbonylphenyl-6'-Me-acridine-9-carboxylate A suspension of acridine-9-carboxylic acid (154 mg, 0.689 mmol) in pyridine (10 mL) was treated with p-toluenesulfonyl chloride (131 mg, 0.689 mmol). The suspension was stirred vigorously under a nitrogen atmosphere until clear and then a solution of methyl 4-hydroxy-3-(2-methoxypropyl)-5-methylbenzoate (82 mg, 0.345 mmol) was added in pyridine (2 mL). The reaction was stirred at room temperature for 3 days. The reaction mixture was evaporated to dryness and the residue was dissolved in chloroform (30 mL). This solution was washed with 1N HCl, saturated aqueous sodium bicarbonate and water. It was then dried over anhydrous magnesium sulfate, filtered and evaporated to dryness. The crude product (167 mg) was purified by preparative TLC on silica using 10% ethyl acetate/chloroform. Yield=29 mg (20%), oily solid. MALDI-TOF MS 443.8 Obs.

g) Synthesis of NSP-2'-(CH₂CH[OMe]Me)-6'-Me-AE

A mixture of 2'-(CH₂CH[OMe]Me)-4'-methoxycarbonylphenyl-6'-Me-acridine 9-carboxylate (29 mg, 66 umoles), 1,3-propane sultone (0.80 g, 100 equivalents) and sodium bicarbonate (55 mg, 10 equivalents) was heated in an oil bath at 140-150° C. After 2 hours the reaction was cooled to room temperature and, a small portion was withdrawn, dissolved in methanol and analyzed by HPLC using a C18 column (4.6×30 mm) and a 30 minute gradient of 10→70% MeCN/water (each containing 0.05% TFA), at a flow rate of 1.0 mL/min and UV-detection at 260 nm. Product was observed eluting at Rt=16.2 minutes. The reaction mixture was diluted with 20 mL of 1:1 ethyl acetate/hexanes. The mixture was sonicated to disperse the gum to a yellow powder and after the powder settled, the solvent was decanted. The yellow powder was rinsed twice with ethyl acetate/hexanes and then dried under vacuum. The crude acridinium ester was suspended in 10 mL of 10% HCl and refluxed under nitrogen. After 2 h, HPLC analysis, showed product from complete hydrolysis of the methyl ester, eluting at Rt=13.7 minutes. (MALDI-TOF MS 643.5 obs.). The crude product was purified by preparative HPLC using a 30×300 mm C18 column and the above gradient at a flow rate of 20 ml/min. The product fraction was collected, frozen at −80° C. and lyophilized to dryness to give a yellow powder.

The following reactions describe the synthesis of NSP-2'-(CH2CH[OMe]Me)-6'-Me-AE.

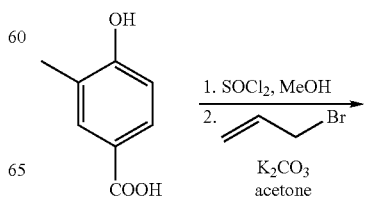

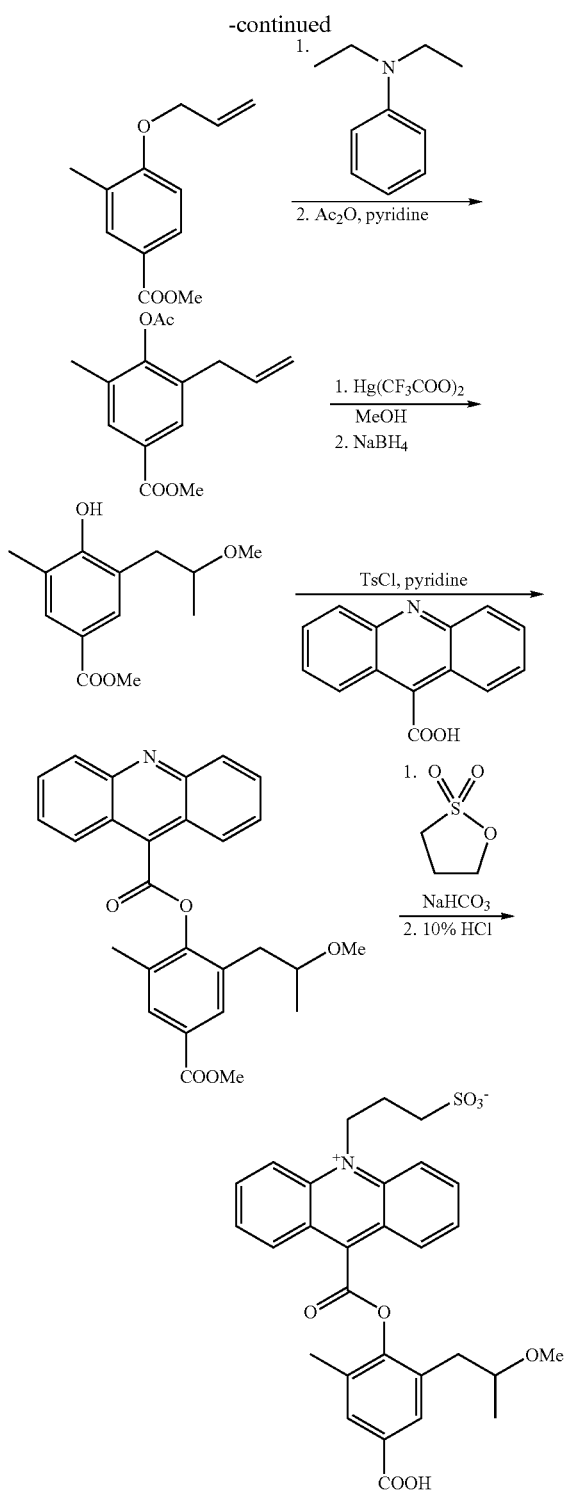

Example 8

Synthesis of NSP-2'-(CH₂CH₂OMe)-6'-Me-AE a) Synthesis of methyl 4-(tert-butyldimethylsilyloxy)-3-allyl-5-methylbenzoate A solution of methyl 4-hydroxy-3-allyl-5-methylbenzoate (157 mg, 0.762 mmol) in dichloromethane (5 mL) was treated with triethylamine (0.21 mL, 2 equivalents) and tert-butyldimethylsilyl chloride (172 mg, 1.5 equivalents). The reaction was stirred at room temperature under a nitrogen atmosphere for 3 days by which time TLC analysis showed complete conversion. The reaction was diluted with ethyl acetate (30 mL) and washed with saturated aqueous ammonium chloride and saturated aqueous sodium bicarbonate. It was then dried over anhydrous magnesium sulfate, filtered and evaporated to dryness to afford the product as a brown oil. Yield=0.239 g (98%).

b) Synthesis of methyl 4-(tert-butyldimethylsilyloxy)-3-(2-hydroxyethyl)-5-methylbenzoate A solution of methyl 4-(tert-butyldimethylsilyloxy)-3-allyl-5-methylbenzoate (0.239 g, 0.742 mmol) in dioxane/water (3:1, 16 mL) was treated with 2,6-lutidine (173 uL, 1.484 mmol), osmium tetroxide (3.8 mg, 0.0148 mmol) which was added as solution in acetone (1 mL) followed by sodium periodate (635 mg, 2.97 mmol). The reaction was stirred at room temperature under a nitrogen atmosphere. After 2 hours, TLC analysis showed mostly product. the reaction was then diluted with ethyl acetate (20 mL) and water (10 mL). The ethyl acetate layer was separated and the aqueous layer was extracted once more with ethyl acetate (10 mL). The combined ethyl acetate extracts were washed with brine. They were then dried over anhydrous magnesium sulfate, filtered and evaporated to dryness. A brown oil (0.255 g) was recovered. The very unstable aldehyde was then reduced immediately by first dissolving it in methanol (5 mL) and after cooling in an ice-bath, adding sodium borohydride (50 mg, 2 equivalents). This reaction was stirred in the ice-bath and after 10 minutes TLC analysis indicated complete conversion to the alcohol. The reaction was then quenched with acetone (2 mL) and stirred for 10 minutes. The reaction mixture was then evaporated to dryness and the residue was dissolved in ethyl acetate (30 mL) and then washed once with saturated aqueous ammonium chloride and then saturated aqueous sodium bicarbonate. The ethyl acetate solution was then dried over anhydrous magnesium sulfate, filtered and evaporated to dryness. A dark brown viscous oil was recovered which was purified by preparative TLC on silica using 25% ethyl acetate.hexanes. The product was obtained as a clear, viscous oil. Yield 138 mg (58%).

c) Synthesis of methyl 4-hydroxy-3-(2-methoxyethyl)-5-methylbenzoate

A solution of methyl 4-(tert-butyldimethylsilyloxy)-3-(2-hydroxyethyl)-5-methylbenzoate (48 mg, 0.148 mmol) in dichloromethane (3 mL) was treated with sodium bicarbonate (60 mg, 4 equivalents) and methyl triflate (68 uL, 4 equivalents). the reaction was stirred at room temperature for 16 h by which time TLC analysis indicated ~50% conversion. The reaction was then diluted with ethyl acetate (20 mL) and filtered. The filtrate was evaporated to dryness. The residue was dissolved in THF (5 mL) and tetrabutylammonium fluoride (60 mg, 1.5 equivalents) was added. The reaction was stirred at room temperature. after 5 minutes, TLC analysis indicated complete conversion. The solvent was removed under educed pressure and the residue was dissolved in ethyl acetate (1 mL) and purified by preparative TLC on silica using 25% ethyl acetate/hexanes. Yield=13 mg (40%).

d) Synthesis of 2'-(CH₂CH₂OMe)-4'-methoxycarbonylphenyl-6'-Me-acridine-9-carboxylate A suspension of acridine-9-carboxylic acid (39 mg, 174 umoles) in pyridine (2 mL) was treated with p-toluenesulfonyl chloride (33 mg, 174 umoles). The reaction was stirred at room temperature under a nitrogen atmosphere for 10-15 minutes until clear and then a solution of methyl 4-hydroxy-3-(2-methoxyethyl)-5-methylbenzoate (13 mg, 58 umoles) was added in pyridine (2 mL). The reaction was stirred at room temperature for 3 days and was then evaporated to dryness. the residue was dissolved in chloroform (25 mL) and washed with saturated aqueous sodium bicarbonate and 10% HCl. It was then dried over anhydrous magnesium sulfate, filtered and evaporated to dryness. Crude Yield 11.3 mg. MALDI-TOF MS 429 obs. This material was used without purification in the next reaction.

e) Synthesis of NSP-2'-(CH$_2$CH$_2$OMe)-6'-Me-AE

A mixture of 2'-(CH$_2$CH$_2$OMe)-4'-methoxycarbonylphenyl-6'-Me-acridine 9-carboxylate (11.3 mg, 26.3 umoles), 1,3-propane sultone (0.642 g, 200 equivalents) and sodium bicarbonate (44 mg, 20 equivalents) was heated in an oil bath at 140-150° C. After 2 hours the reaction was cooled to room temperature and, a small portion was withdrawn, dissolved in methanol and analyzed by HPLC using a C18 column (4.6× 30 mm) and a 30 minute gradient of 10→70% MeCN/water (each containing 0.05% TFA), at a flow rate of 1.0 mL/min and UV-detection at 260 nm. Product was observed eluting at Rt=15.8 minutes. The reaction mixture was diluted with 20 mL of 1:1 ethyl acetate/hexanes. The mixture was sonicated to disperse the gum to a yellow powder and after the powder settled, the solvent was decanted. The yellow powder was rinsed twice with ethyl acetate/hexanes and then dried under vacuum. The crude acridinium ester was suspended in 10 mL of 10% HCl and refluxed under nitrogen. After 2 h, HPLC analysis, showed product from complete hydrolysis of the methyl ester, eluting at Rt=14.0 minutes. (MALDI-TOF MS 537.9 obs.). The crude product was purified by preparative HPLC using a 30×300 mm C18 column and the above gradient at a flow rate of 20 ml/min. The product fraction was collected, frozen at −80° C. and lyophilized to dryness to give a yellow powder.

The following reactions describe the synthesis of NSP-2'-(CH$_2$CH$_2$OMe)-6'-Me-AE.

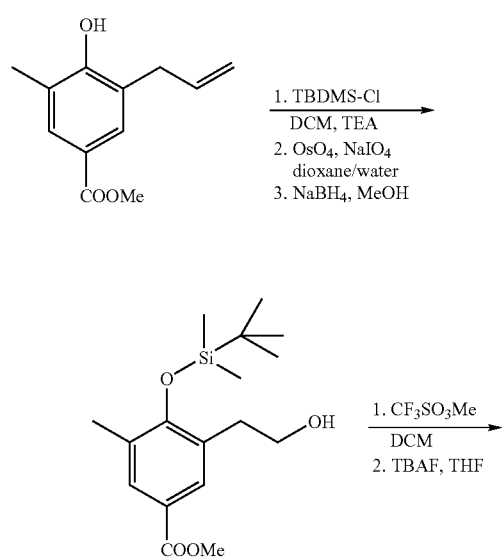

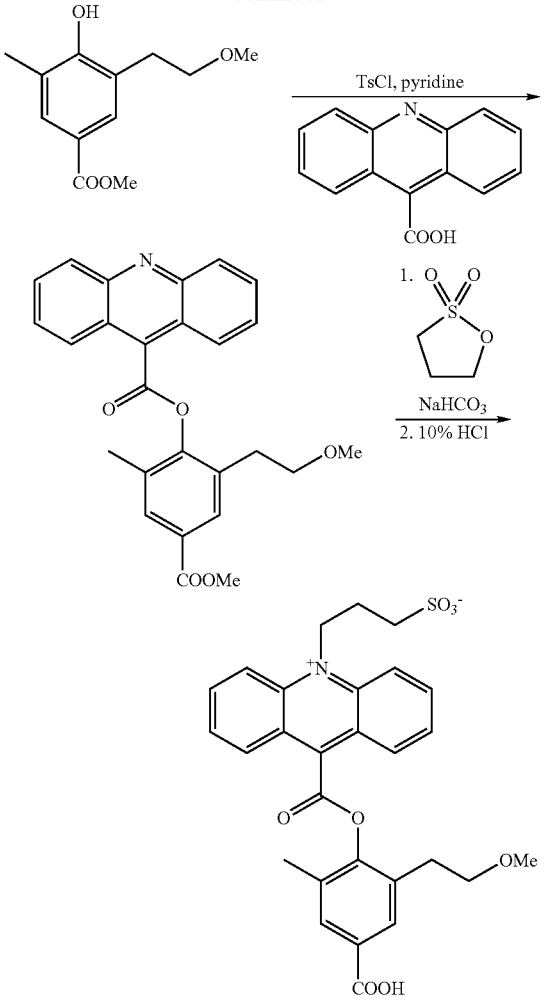

Example 9

General Procedure for Labeling Anti-TSH Mab with Acridinium Ester

A stock solution of the antibody (5 mg/mL, 200 uL, 1 mg, 6.67 nmoles) was diluted with 0.1 M phosphate buffer pH 8 (300 uL) and cooled to 4° C. in a cold box. To this cold solution was added 10 equivalents of the acridinium NHS ester as a DMF solution (1 mg/mL). For example, in the case of NSP-DMAE-NHS, 39.4 uL (66.7 nmoles) was added to the protein solution.

The labeling reactions were stirred gently at room temperature for 3-4 hours and were then diluted with de-ionized water (1.5 mL). These diluted solutions were then transferred to 2 mL Centricon™ filters (MW 30,000 cutoff) and centrifuged at 4500G to reduce the volume to ~0.2 mL. This process was repeated three more times. The filtered conjugates were finally diluted into a total volume of 0.5 mL de-ionized water for mass spectral analysis and RLU measurements.

Mass spectra were recorded on a Voyager DE MALDI-TOF mass spectrometer and the unlabeled antibody was used as the reference. Approximately 2 uL of the conjugate solution was mixed with 2 uL of sinnapinic acid matrix solution (HP) and the spotted on a MALDI plate. After complete drying, mass spectra were recorded. From the difference in mass values for the unlabeled antibody and the conjugates, the extent of AE incorporation could be measured. Typically, under these labeling conditions, 2-4 AE labels were incorporated in the antibody.

Example 10

General Procedure for Light Measurements

All light measurements were performed on either a MLA1™ or MLA2™ (AE stability measurements), Bayer Diagnostics. For measurement of RLUs from the acridinium esters, 1 mg/mL DMF solutions of the HPLC-purified compounds were sequentially diluted $10^6$-$10^7$-fold into 10 mM phosphate, 150 mM NaCl pH 8 also containing 0.05% BSA and 0.1% sodium azide. The protein conjugates and the HPLC-purified cortisol conjugates were diluted in the same manner. Light measurements used 25 uL of sample and were initiated in the instrument with the addition of 0.350 mL of reagent 1 which contained 0.5% hydrogen peroxide in 0.1 N nitric acid followed by the addition of 0.35 mL reagent 2 which contained a surfactant in 0.25 N NaOH. A very short delay time of 0.1 s was used between addition of reagent 1 and reagent 2. For the kinetics measurements, the measuring time was varied from 0.5 s to 10 s for the acridinium esters and 0.5 s to 5 s for the protein and cortisol conjugates. The amount of light emitted at each measuring time was reported as RLUs by the instruments, which were then converted to percentages by assigning a value of 100% for the RLUs recorded at 10 s for the acridinium esters and 5 s for the conjugates. For the AE stability measurements, a measuring time of 5 seconds was used.

We claim:

1. A hydrolytically stable, fast light emitting chemiluminescent acridinium ester comprising the structure of Formula I:

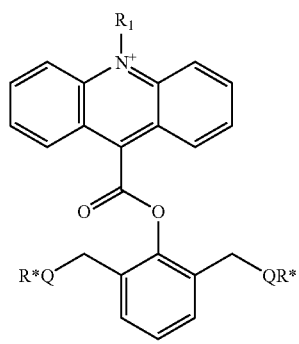

I wherein Q is selected independently at each occurrence from a bond, —O—, —S—, or —N(R*)—; wherein R* is selected independently at each occurrence from hydrogen, substituted or unsubstituted, branched or straight chain alkyl, alkenyl, alkynyl, aryl, alkyl-aryl, or aryl-alkyl, and combinations thereof, optionally containing from one to 20 heteroatoms selected from the group consisting of oxygen, nitrogen, phosphorous, sulfur, halogen, and combinations thereof; with the proviso that at least one Q must be —O—, —S—, or —N(R*)—; wherein $R_1$ is an alkyl, alkenyl, alkynyl, aryl-alkyl or alkyl-aryl group containing up to 20 heteroatoms.

2. The hydrolytically stable, fast light emitting chemiluminescent acridinium ester of claim 1, wherein one Q represents —O— and the other Q represents a bond.

3. The hydrolytically stable, fast light emitting chemiluminescent acridinium ester of claim 1, wherein one Q represents —O— and the other Q represents a bond and wherein R* is methyl.

4. The hydrolytically stable, fast light emitting chemiluminescent acridinium ester of claim 1, wherein both instances of Q represent —O—.

5. A hydrolytically stable, fast light emitting chemiluminescent acridinium ester comprising the structure of Formula II:

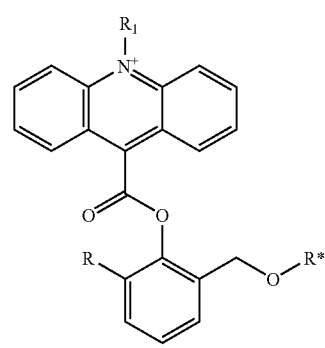

II wherein R and R* are selected independently from hydrogen, substituted or unsubstituted, branched or straight chain alkyl, alkenyl, alkynyl, aryl, alkyl-aryl, or aryl-alkyl, and combinations thereof, optionally containing from one to 20 heteroatoms selected from the group consisting of oxygen, nitrogen, phosphorous, sulfur, halogen, and combinations thereof; and wherein $R_1$ is an alkyl, alkenyl, alkynyl, aryl-alkyl or alkyl-aryl group containing up to 20 heteroatoms.

6. The hydrolytically stable, fast light emitting chemiluminescent acridinium ester of claim 5, wherein R is methyl.

7. A hydrolytically stable, fast light emitting chemiluminescent acridinium ester comprising the structure of Formula III:

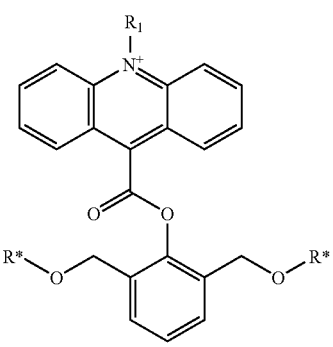

III wherein R* is selected independently at each occurrence from hydrogen, substituted or unsubstituted, branched or straight chain alkyl, alkenyl, alkynyl, aryl, alkyl-aryl, or aryl-alkyl, and combinations thereof, optionally containing from one to 20 heteroatoms selected from the group consisting of oxygen, nitrogen, phosphorous, sulfur, halogen, and combinations thereof; and wherein $R_1$ is an alkyl, alkenyl, alkynyl, aryl-alkyl or alkyl-aryl group containing up to 20 heteroatoms.

8. A hydrolytically stable, fast light emitting chemiluminescent acridinium ester of Formula IV:

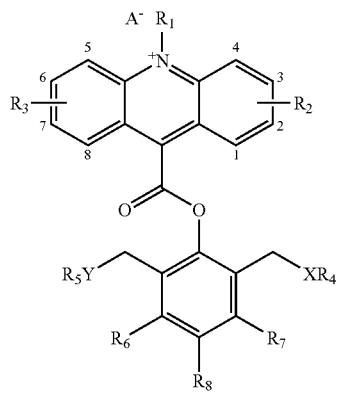

wherein,
- $R_1$ is an alkyl, alkenyl, alkynyl, aryl-alkyl or alkyl-aryl group containing up to 20 heteroatoms;
- $R_2$ is a functional group at any of $C_1$ to $C_4$ and $R_3$ is functional group at any of $C_5$ to $C_8$;
- $R_2$ and $R_3$ are independently selected from hydrogen, alkyl, alkenyl, alkynyl, aryl, aryl-alkyl or alkyl-aryl groups containing up to 20 heteroatoms selected from oxygen, nitrogen, sulfur or halogen;
- X and Y are selected independently at each occurrence from a bond, —O—, —S—, or —N(R*)—; wherein R* is selected independently at each occurrence from hydrogen, substituted or unsubstituted, branched or straight chain alkyl, alkenyl, alkynyl, aryl, alkyl-aryl, or aryl-alkyl, and combinations thereof, optionally containing from one to 20 heteroatoms selected from the group consisting of oxygen, nitrogen, phosphorous, sulfur, halogen, and combinations thereof; with the proviso that either X or Y or both must be —O—, —S—, or —N(R*)—;
- $R_4$ and $R_5$ are independently selected from hydrogen, alkyl, alkenyl, alkynyl, aryl, aryl-alkyl or alkyl-aryl groups containing up to 20 heteroatoms selected from oxygen, nitrogen, sulfur or halogen;
- $R_6$ and $R_7$ are independently selected from hydrogen, alkyl, alkenyl, alkynyl, aryl-alkyl, alkyl-aryl, alkoxyl (—OR), alkylthiol (—SR), and —NR$_2$ groups where R on the nitrogen can be the same or different and is an alkyl, alkenyl, alkynyl, aryl, aryl-alkyl or alkyl-aryl group containing up to 20 heteroatoms;
- $R_8$ is a group exchangeable with $R_6$ and $R_7$ and is group —$R_9$-$R_{10}$;
- $R_9$ represents a bond or a substituted or unsubstituted, branched or straight-chain alkyl, aryl, aryl-alkyl or alkyl-aryl group containing up to 20 heteroatoms;
- $R_{10}$ is a electrophilic or nucleophilic functional group selected from the following:

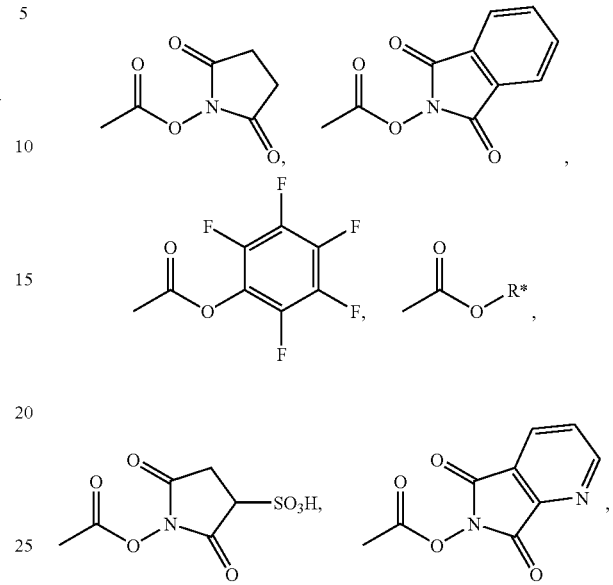

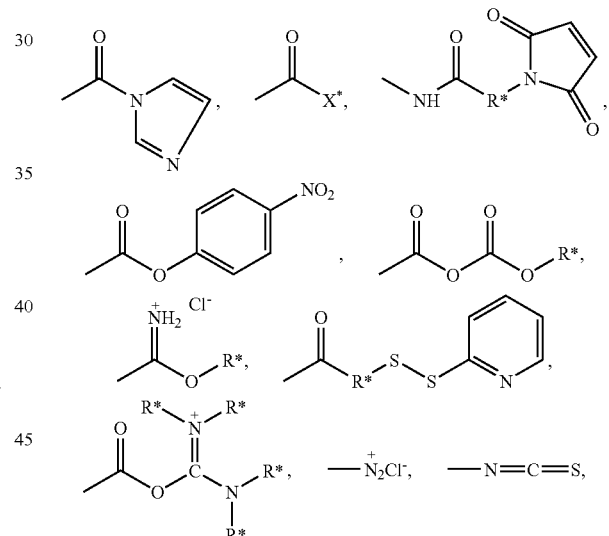

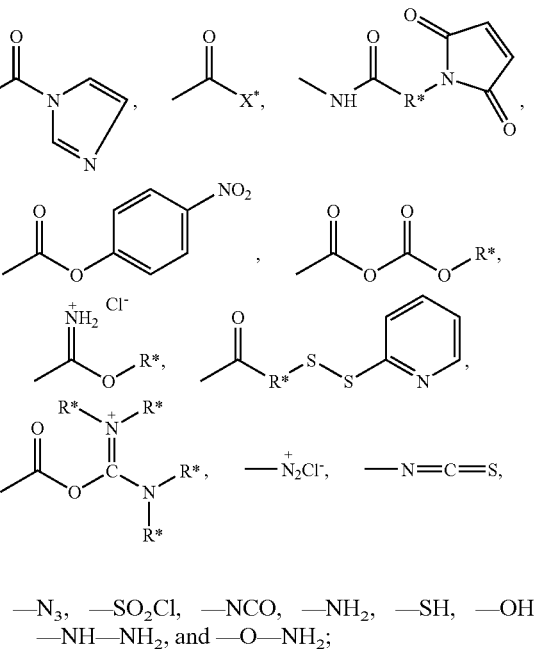

—$N_3$, —$SO_2Cl$, —NCO, —$NH_2$, —SH, —OH, —NH—$NH_2$, and —O—$NH_2$;

wherein X* is a halogen; and R* is selected from the group consisting of hydrogen, substituted or unsubstituted, branched or straight chain alkyl, alkenyl, alkynyl, aryl, alkyl-aryl, or aryl-alkyl, and combinations thereof, optionally containing one or more heteroatoms selected from the group consisting of oxygen, nitrogen, phosphorous, sulfur, halogen, and combinations thereof; and A⁻ is a counter ion which is paired with the quaternary nitrogen of said acridinium nucleus.

9. The hydrolytically stable, fast light emitting chemiluminescent acridinium ester of claim 8 wherein $R_1$ is a methyl, sulfopropyl, or sulfobutyl group.

10. The hydrolytically stable, fast light emitting chemiluminescent acridinium ester of claim 8 having the structure:

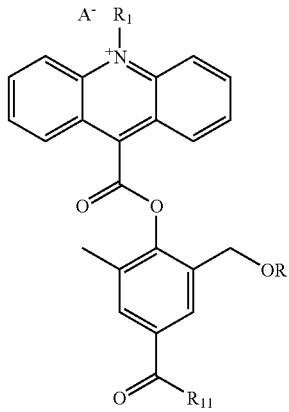

where $R_1$ is -Me or —$CH_2CH_2CH_2SO_3^-$;
R is an alkyl, alkenyl, alkynyl, aryl, aryl-alkyl or alkyl-aryl group containing up to 20 heteroatoms,
$R_{11}$ is —OH, —O—N-succinimidyl, —NH—$(CH_2)_5$—C(O)—O—N-succinimidyl, —NH—$(C_2H_4O)_n$—$C_2H_4$NH—C(O)—O—N-succinimidyl wherein n=0 to 5, or —NH—R—NHR; and
$A^-$ is a counter ion which is introduced to pair with the quaternary nitrogen of said acridinium nucleus in the case where $R_1$ is -Me, and is selected from the group consisting of $CH_3SO_4^-$, $FSO_3^-$, $CF_3SO_4^-$, $C_4F_9SO_4^-$, $CH_3C_6H_4SO_3^-$, halide, $CF_3COO^-$, $CH_3COO^-$, and $NO_3^-$.

11. The hydrolytically stable, fast light emitting chemiluminescent acridinium ester of claim 8 having the structure:

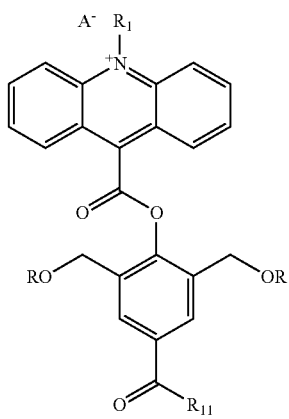

where $R_1$ is -Me or —$CH_2CH_2CH_2SO_3^-$;
R is an alkyl, alkenyl, alkynyl, aryl, aryl-alkyl or alkyl-aryl group containing up to 20 heteroatoms,
$R_{11}$ is —OH, —O—N-succinimidyl, —NH—$(CH_2)_5$—C(O)—O—N-succinimidyl, —NH—$(C_2H_4O)_n$—$C_2H_4$NH—C(O)—O—N-succinimidyl wherein n=0 to 5, or —NH—R—NHR; and
$A^-$ is a counter ion which is introduced to pair with the quaternary nitrogen of said acridinium nucleus in the case where $R_1$ is -Me, and is selected from the group consisting of $CH_3SO_4^-$, $FSO_3^-$, $CF_3SO_4^-$, $C_4F_9SO_4^-$, $CH_3C_6H_4SO_3^-$, halide, $CF_3COO^-$, $CH_3COO^-$, and $NO_3^-$.

12. The hydrolytically stable, fast light emitting chemiluminescent acridinium ester of claim 8 having the structure:

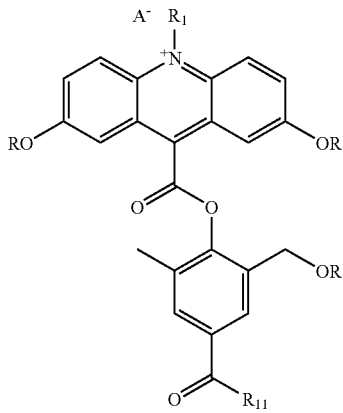

where $R_1$ is -Me or —$CH_2CH_2CH_2SO_3^-$;
R is an alkyl, alkenyl, alkynyl, aryl, aryl-alkyl or alkyl-aryl group containing up to 20 heteroatoms,
$R_{11}$ is —OH, —O—N-succinimidyl, —NH—$(CH_2)_5$—C(O)—O—N-succinimidyl, —NH—$(C_2H_4O)_n$—$C_2H_4$NH—C(O)—O—N-succinimidyl wherein n=0 to 5, or —NH—R—NHR; and
$A^-$ is a counter ion which is introduced to pair with the quaternary nitrogen of said acridinium nucleus in the case where $R_1$ is -Me, and is selected from the group consisting of $CH_3SO_4^-$, $FSO_3^-$, $CF_3SO_4^-$, $C_4F_9SO_4^-$, $CH_3C_6H_4SO_3^-$, halide, $CF_3COO^-$, $CH_3COO^-$, and $NO_3^-$.

13. The hydrolytically stable, fast light emitting chemiluminescent acridinium ester of claim 8 having the structure:

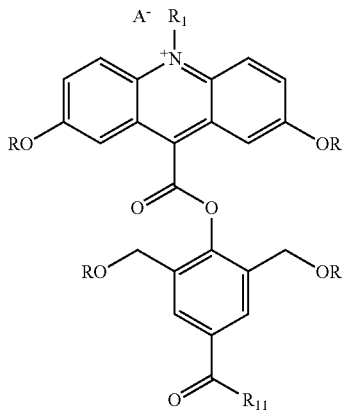

where $R_1$ is -Me or —$CH_2CH_2CH_2SO_3^-$;
R is an alkyl, alkenyl, alkynyl, aryl, aryl-alkyl or alkyl-aryl group containing up to 20 heteroatoms,
$R_{11}$ is —OH, —O—N-succinimidyl, —NH—$(CH_2)_5$—C(O)—O—N-succinimidyl, —NH—$(C_2H_4O)_n$—$C_2H_4$NH—C(O)—O—N-succinimidyl where n=0 to 5, or —NH—R—NHR; and
$A^-$ is a counter ion which is introduced to pair with the quaternary nitrogen of said acridinium nucleus in the case where $R_1$ is -Me, and is selected from the group consisting of $CH_3SO_4^-$, $FSO_3^-$, $CF_3SO_4^-$, $C_4F_9SO_4^-$, $CH_3C_6H_4SO_3^-$, halide, $CF_3COO^-$, $CH_3COO^-$, and $NO_3^-$.

14. The hydrolytically stable, fast light emitting chemiluminescent acridinium ester of claim 8 having the structure:

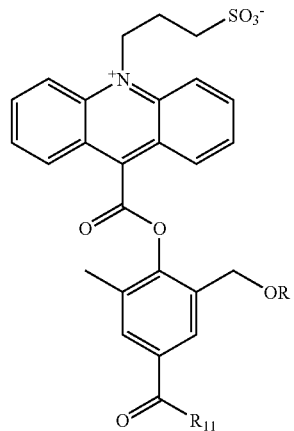

where R is selected from -Me, —CH₂CH₂OMe, —CHMe₂ and —(CH₂CH₂O)$_n$CH₂CH₂OMe, —CH[CH₂—O—(CH₂CH₂O)$_n$CH₂CH₂OMe]₂, n=1-5 and $R_{11}$ is —OH, —O—N-succinimidyl, —NH—(CH₂)₅—C(O)—O—N-succinimidyl, —NH—(C₂H₄O)$_n$—C₂H₄NH—C(O)—O—N-succinimidyl where n=0 to 5, or —NH—R—NHR.

15. The hydrolytically stable, fast light emitting chemiluminescent acridinium ester of claim 8 having the structure:

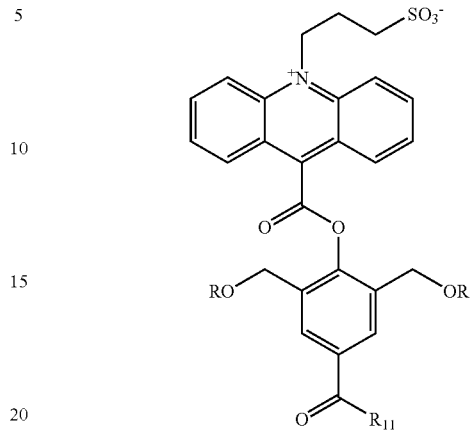

where R is selected from -Me, —CH₂CH₂OMe, —CHMe₂ and —(CH₂CH₂O)$_n$CH₂CH₂OMe, —CH[CH₂—O—(CH₂CH₂O)$_n$CH₂CH₂OMe]₂, n=1-5 and $R_{11}$ is —OH, —O—N-succinimidyl, —NH—(CH₂)₅—C(O)—O—N-succinimidyl, —NH—(C₂H₄O)$_n$—C₂H₄NH—C(O)—O—N-succinimidyl where n=0 to 5, or —NH—R—NHR.

16. The hydrolytically stable, fast light emitting chemiluminescent acridinium ester of claim 8 having the structure:

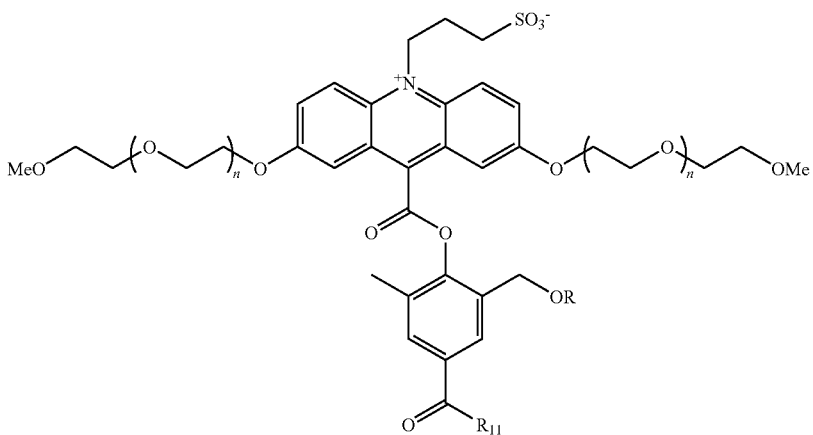

where R is selected from -Me, —CH₂CH₂OMe, —CHMe₂-(CH₂CH₂O)$_n$CH₂CH₂OMe, and —CH[CH₂—O—(CH₂CH₂O)$_n$CH₂CH₂OMe]₂, where n=1-5 and $R_{11}$ is —OH, —O—N-succinimidyl, —NH—(CH₂)₅—C(O)—O—N-succinimidyl, —NH—(C₂H₄O)$_n$—C₂H₄NH—C(O)—O—N-succinimidyl where n=0 to 5, or —NH—R—NHR.

17. The hydrolytically stable, fast light emitting chemiluminescent acridinium ester of claim 8 having the structure:

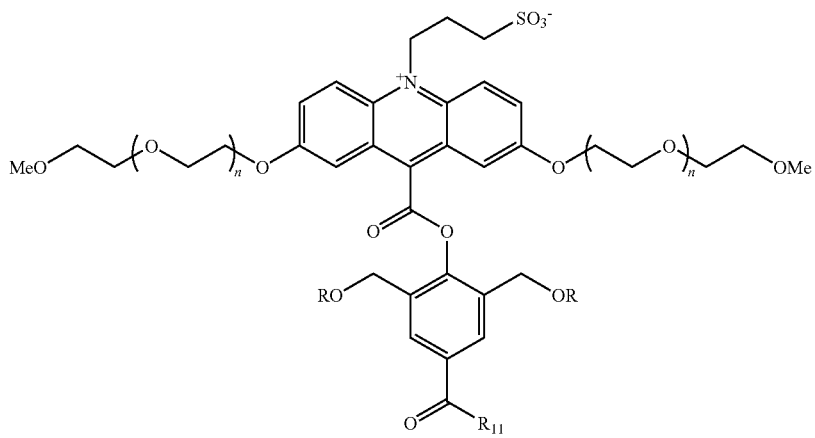

where R is selected from -Me, —CH$_2$CH$_2$OMe, —CHMe$_2$-(CH$_2$CH$_2$O)$_n$CH$_2$CH$_2$OMe, and —CH[CH$_2$—O—(CH$_2$CH$_2$O)$_n$CH$_2$CH$_2$OMe]$_2$, where n=1-5 and R$_{11}$ is —OH, —O—N-succinimidyl, —NH—(CH$_2$)$_5$—C(O)—O—N-succinimidyl, —NH—(C$_2$H$_4$O)$_n$—C$_2$H$_4$NH—C(O)—O—N-succinimidyl where n=0 to 5, or —NH—R—NHR.

18. An assay for the detection or quantification of an analyte comprises the steps of:

(a) providing a conjugate comprising: (i) a binding molecule specific for an analyte; and (ii) a hydrolytically stable, fast light emitting acridinium ester according to claim 1;

(b) providing a solid support having immobilized thereon a second binding molecule specific for said analyte;

(c) mixing the conjugate, the solid phase and a sample suspected of containing the analyte to form a binding complex;

(d) separating the binding complex captured on the solid support;

(e) triggering chemiluminescence of the binding complex from step (d) by adding chemiluminescence triggering reagents;

(f) measuring the amount of light emission with a luminometer; and (g) detecting the presence or calculating the concentration of the analyte by comparing the amount of light emitted from the reaction mixture with a standard dose response curve which relates the amount of light emitted to a known concentration of the analyte.

19. An assay for the detection or quantification of an analyte comprises the steps of:

(a) providing a conjugate of an analyte with a hydrolytically stable, fast light emitting acridinium ester according to claim 1;

(b) providing a solid support immobilized with a binding molecule specific for the analyte;

(c) mixing the conjugate, solid support and a sample suspected of containing the analyte to form a binding complex;

(d) separating the binding complex captured on the solid support;

(e) triggering the chemiluminescence of the binding complex from step (d) by adding chemiluminescence triggering reagents;

(f) measuring the amount of light with an luminometer; and (g) detecting the presence or calculating the concentration of the analyte by comparing the amount of light emitted from the reaction mixture with a standard dose response curve which relates the amount of light emitted to a known concentration of the analyte.

20. A conjugate of the acridinium esters of claim 8 to an analyte.

21. The conjugate of claim 20 wherein the analyte is a small molecule analytes selected from steroids, vitamins, hormones, therapeutic drugs, and small peptides.

22. The conjugate of claim 20 wherein the analyte is a macromolecular analyte selected from proteins, nucleic acids, oligosaccharides, antibodies, antibody fragments, cells, viruses, and synthetic polymers.

23. A binding molecule of claim 8 wherein the binding molecule is selected from an antibody, an antibody fragment, a binding protein, a nucleic acid, a peptide, a receptor or a synthetic binding molecule.

* * * * *